(12) United States Patent
Hartmann et al.

(10) Patent No.: US 9,963,499 B2
(45) Date of Patent: May 8, 2018

(54) EXPRESSION OF MONOCLONAL ANTIBODIES IN CILIATE HOST CELLS

(75) Inventors: Marcus Hartmann, Münster (DE); Jenny Apelt, Münster (DE)

(73) Assignee: CILIAN AG, Munster (DE)

( * ) Notice: Subject to any disclaimer, the term of this patent is extended or adjusted under 35 U.S.C. 154(b) by 426 days.

(21) Appl. No.: 13/582,633

(22) PCT Filed: Mar. 2, 2011

(86) PCT No.: PCT/EP2011/053129
§ 371 (c)(1),
(2), (4) Date: Nov. 19, 2012

(87) PCT Pub. No.: WO2011/107520
PCT Pub. Date: Sep. 9, 2011

(65) Prior Publication Data
US 2013/0109593 A1 May 2, 2013

(30) Foreign Application Priority Data

Mar. 5, 2010 (GB) .................................. 1003701.8

(51) Int. Cl.
*C07K 16/00* (2006.01)
*C07K 16/28* (2006.01)
*C07K 16/46* (2006.01)
*C40B 40/10* (2006.01)

(52) U.S. Cl.
CPC .......... *C07K 16/00* (2013.01); *C07K 16/2812* (2013.01); *C07K 16/468* (2013.01); *C07K 2317/10* (2013.01); *C07K 2317/41* (2013.01); *C07K 2317/72* (2013.01); *C40B 40/10* (2013.01)

(58) Field of Classification Search
None
See application file for complete search history.

(56) References Cited

U.S. PATENT DOCUMENTS

| | | | |
|---|---|---|---|
| 2,048,621 A | 7/1936 | Potts | 400/463 |
| 5,223,409 A | 6/1993 | Ladner | 435/69.7 |
| 5,859,205 A | 1/1999 | Adair | 424/130.1 |
| 6,087,124 A | 7/2000 | Steinbruck | 435/69.1 |
| 6,248,516 B1 | 6/2001 | Winter | 435/6 |
| 6,300,064 B1 | 10/2001 | Knappik | 435/69.1 |
| 6,331,415 B1 | 12/2001 | Cabilly | 435/326 |

(Continued)

FOREIGN PATENT DOCUMENTS

| | | |
|---|---|---|
| CA | 2755973 A1 | 9/2010 |
| CA | 28288131 | 9/2011 |

(Continued)

OTHER PUBLICATIONS

Aldag I, et al. Expression, secretion and surface display of a human alkaline phosphatase by the ciliate Tetrahymena thermophila, BMC Biotechnol 11:11 (11 pages) (2011).

(Continued)

*Primary Examiner* — Christian C Boesen
(74) *Attorney, Agent, or Firm* — Ballard Spahr LLP

(57) ABSTRACT

The present invention is related to a system for the heterologous expression of a monoclonal Antibody (mAb) or a fragment or derivative thereof, said system comprising at least one ciliate host cell, and incorporated, into said ciliate host cell, at least one heterologous nucleic acid molecule encoding for said monoclonal Antibody, or a fragment or derivative thereof.

4 Claims, 10 Drawing Sheets

(56) References Cited

U.S. PATENT DOCUMENTS

Figure 1:
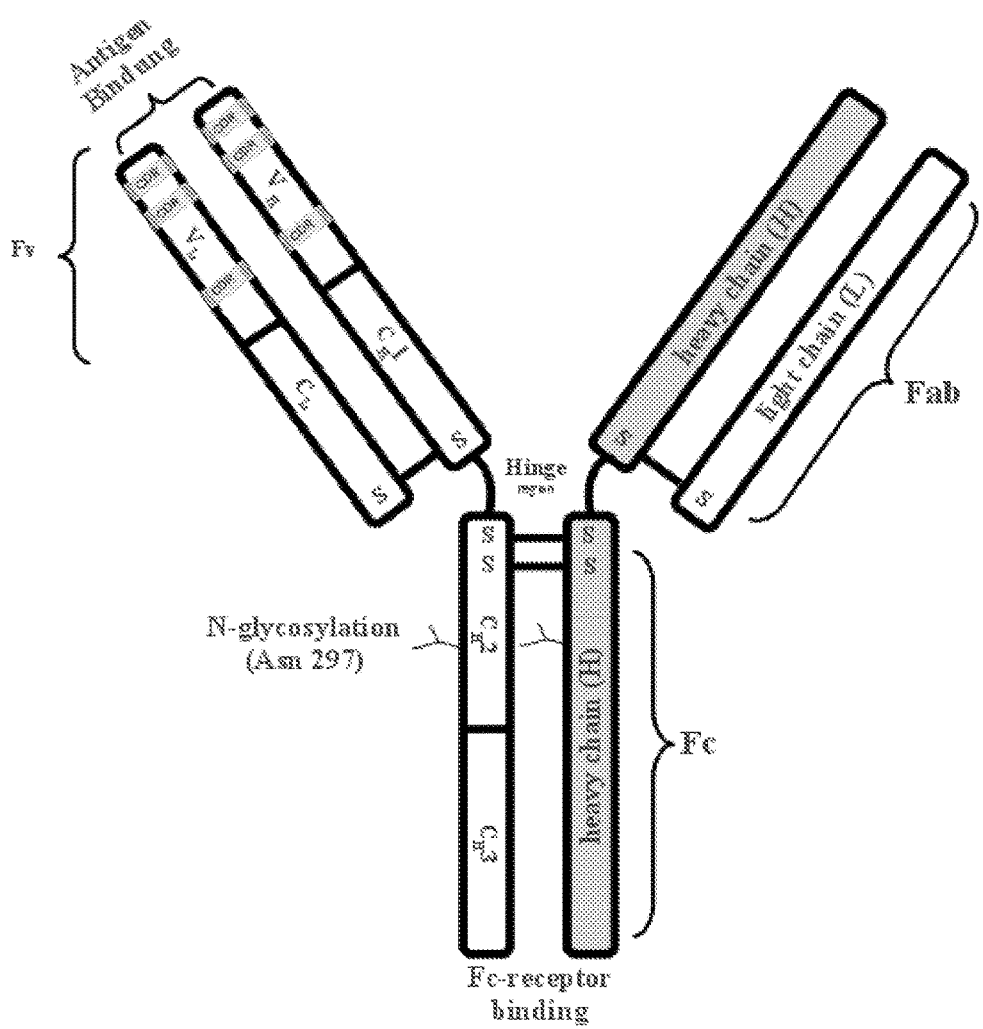

| | | | |
|---|---|---|---|
| 6,548,640 | B1 | 4/2003 | Winter .................. 530/387.1 |
| 6,846,481 | B1 | 1/2005 | Gaertig .................. 424/191.1 |
| 2003/0219869 | A1 | 11/2003 | Kiy .................. 435/6 |
| 2003/0219900 | A1 | 11/2003 | Rusing .................. 435/183 |

FOREIGN PATENT DOCUMENTS

| | | |
|---|---|---|
| CN | 101627111 | 1/2010 |
| CN | 102884078 A | 1/2013 |
| EP | 0590058 A1 | 4/1994 |
| EP | 1176195 | 1/2002 |
| EP | 2542575 A1 | 1/2013 |
| GB | 1003701.8 | 3/2010 |
| JP | 5984680 B2 | 9/2016 |
| KR | 20120131201 A | 12/2012 |
| WO | WO 92/22653 | 12/1992 |
| WO | WO 00/46381 | 8/2000 |
| WO | WO 00/58483 | 10/2000 |
| WO | WO 03/078566 | 9/2003 |
| WO | WO 2007/006812 | 1/2007 |
| WO | WO 2007/028106 | 3/2007 |
| WO | WO 2010/108182 | 9/2010 |
| WO | WO 2011/107520 | 9/2011 |
| WO | WO 2011/116387 | 9/2011 |

OTHER PUBLICATIONS

Banno Y, et al. Purification and characterization of a secreted protease from Tetrahymena pyriformis, Eur J Biochem 132, pp. 563-568 (1983).

Gaertig J & Gorovsky MA. Efficient mass transformation of Tetrahymena thermophila by electroporation of conjugants, PNAS 89, pp. 9196-9200 (1992).

Gerngross TU. Advances in the production of human therapeutic proteins in yeasts and filamentous fungi, Nat Biotech 22, pp. 1409-1414 (2004).

Herrmann L, et al. The bifunctional dihydrofolate reductase thymidylate synthase of Tetrahymena thermophila provides a tool for molecular and biotechnology applications, BMC Biotechnol 6:21 (11 pages) (2006).

Kufer P, et al. A revival of bispecific antibodies, Trends Biotechnol 22, pp. 238-244 (2004).

Ruf P & Lindhofer H. Induction of a long-lasting antitumor immunity by a trifunctional bispecific antibody, Blood 98, pp. 2526-2534 (2001).

Shields RL, et al. Lack of fucose on human IgG N-Linked oligosaccharide improves binding to human Fc RIII and antibody-dependent cellular toxicity, J Biol Chem 277, pp. 26733-26740 (2002).

Tondravi MM & Yao MC. Transformation of Tetrahymena thermophila by microinjection of ribosomal RNA genes, PNAS 83, pp. 4369-4373 (1996).

Wei Y, et al. Glyco-engineering of human IgG1-Fc through combined yeast expression and in vitro chemoenzymatic glycosylation, Biochemistry 47, pp. 10294 (2008).

Weide T, et al. A recombinase system facilitates cloning of expression cassettes in the ciliate Tetrahymena thermophila, BMC Microbiol 7:12 (11 pages) (2007).

Weide T, et al. Secretion of functional human enzymes by Tetrahymena thermophila, BMC Biotechnol 6:19 (9 pages) (2006).

Written Opinion issued Sep. 5, 2012 by the International Searching Authority for application PCT/EP2011/053129 filed Mar. 2, 2011, which later published as 2011/107520 (Applicant—Cilian AG // 1st Named Inventor—Hartmann) (6 pages).

International Search Report issued May 13, 2011 by the International Searching Authority for application PCT/EP2011/053129 filed Mar. 2, 2011, which later published as 2011/107520 (Applicant—Cilian AG // 1st Named Inventor—Hartmann) (5 pages).

International Preliminary Report on Patentability issued Sep. 11, 2012 by the International Bureau for application PCT/EP2011/053129, which later published as 2011/107520 filed Mar. 2, 2011 (Applicant—Cilian AG // 1st Named Inventor—Hartmann) (7 pages).

Chames, et al., "Bispecific antibodies for cancer therapy" Current Opinion in Drug Discovery & Development 2009 12(2): (15 pages).

Hollander, N., "Bispecific antibodies for cancer therapy" Immunotherapy (2009) 1(2), 211-222.

Office Action dated Dec. 21, 2016 by the Canadian Patent Office for CA Application No. 2,828,131, filed Feb. 3, 2011 and published as 2828131 on Sep. 9, 2011 (Applicant—Cilian AG) (5 pages).

Response to Office Action dated Feb. 17, 2017 by the Canadian Patent Office for CA Application No. 2,828,131, filed Feb. 3, 2011 and published as 2828131 on Sep. 9, 2011 (Applicant—Cilian AG) (34 pages).

*Tetrahymena thermophila* [gbinv]: 283 CDS's (145922 codons)

fields: [triplet] [frequency: per thousand] ([number])

```
UUU 26.1(  3815)   UCU 24.4(  3557)   UAU 23.3(  3407)   UGU  9.7(  1412)
UUC 19.4(  2827)   UCC  6.5(   948)   UAC 14.5(  2110)   UGC  8.8(  1282)
UUA 29.8(  4346)   UCA 16.8(  2453)   UAA 36.8(  5366)   UGA  2.0(   286)
UUG 14.1(  2054)   UCG  1.5(   222)   UAG 11.0(  1606)   UGG  7.4(  1080)

CUU 20.3(  2955)   CCU 17.6(  2574)   CAU  8.7(  1267)   CGU  4.6(   677)
CUC 10.3(  1497)   CCC  4.6(   676)   CAC  6.4(   930)   CGC  0.9(   136)
CUA  7.4(  1078)   CCA  8.2(  1202)   CAA 19.8(  2894)   CGA  0.5(    73)
CUG  2.6(   378)   CCG  0.5(    68)   CAG  3.3(   477)   CGG  0.1(     8)

AUU 39.3(  5733)   ACU 27.2(  3968)   AAU 48.0(  7002)   AGU 13.5(  1963)
AUC 16.2(  2367)   ACC  7.8(  1140)   AAC 24.2(  3530)   AGC  9.2(  1344)
AUA 19.1(  2783)   ACA 14.8(  2153)   AAA 58.7(  8562)   AGA 26.6(  3887)
AUG 19.3(  2811)   ACG  0.8(   111)   AAG 34.3(  5001)   AGG  2.8(   412)

GUU 25.8(  3763)   GCU 30.3(  4428)   GAU 42.5(  6208)   GGU 24.5(  3576)
GUC 10.1(  1469)   GCC  7.5(  1098)   GAC 12.4(  1815)   GGC  4.3(   629)
GUA 11.6(  1693)   GCA 11.8(  1726)   GAA 58.2(  8499)   GGA 15.1(  2205)
GUG  3.1(   451)   GCG  0.6(    88)   GAG 11.2(  1630)   GGG  1.5(   216)
```

Coding GC 32.53% 1st letter GC 38.64% 2nd letter GC 31.25% 3rd letter GC 27.69%

*Homo sapiens* [gbpri]: 93487 CDS's (40662582 codons)

fields: [triplet] [frequency: per thousand] ([number])

```
UUU 17.6(714298)   UCU 15.2(618711)   UAU 12.2(495699)   UGU 10.6(430311)
UUC 20.3(824692)   UCC 17.7(718892)   UAC 15.3(622407)   UGC 12.6(513028)
UUA  7.7(311881)   UCA 12.2(496448)   UAA  1.0( 40285)   UGA  1.6( 63237)
UUG 12.9(525688)   UCG  4.4(179419)   UAG  0.8( 32109)   UGG 13.2(535595)

CUU 13.2(536515)   CCU 17.5(713233)   CAU 10.9(441711)   CGU  4.5(184609)
CUC 19.6(796638)   CCC 19.8(804620)   CAC 15.1(613713)   CGC 10.4(423516)
CUA  7.2(290751)   CCA 16.9(688038)   CAA 12.3(501911)   CGA  6.2(250760)
CUG 39.6(1611801)  CCG  6.9(281570)   CAG 34.2(1391973)  CGG 11.4(464485)

AUU 16.0(650473)   ACU 13.1(533609)   AAU 17.0(689701)   AGU 12.1(493429)
AUC 20.8(846466)   ACC 18.9(768147)   AAC 19.1(776603)   AGC 19.5(791383)
AUA  7.5(304565)   ACA 15.1(614523)   AAA 24.4(993621)   AGA 12.2(494682)
AUG 22.0(896005)   ACG  6.1(246105)   AAG 31.9(1295568)  AGG 12.0(486463)

GUU 11.0(448607)   GCU 18.4(750096)   GAU 21.8(885429)   GGU 10.8(437126)
GUC 14.5(588138)   GCC 27.7(1127679)  GAC 25.1(1020595)  GGC 22.2(903565)
GUA  7.1(287712)   GCA 15.8(643471)   GAA 29.0(1177632)  GGA 16.5(669873)
GUG 28.1(1143534)  GCG  7.4(299495)   GAG 39.6(1609975)  GGG 16.5(669768)
```

Coding GC 52.27% 1st letter GC 55.72% 2nd letter GC 42.54% 3rd letter GC 58.55%

Fig. 9

| 1LC | 3LC | amino acid | Codons | | | | | |
|---|---|---|---|---|---|---|---|---|
| A | Ala | Alanine | GCU | GCA | GCC | GCG | | |
| C | Cys | Cysteine | UGU | UGC | | | | |
| D | Asp | Aspartic acid | GAU | GAC | | | | |
| E | Glu | Glutamic acid | GAA | GAG | | | | |
| F | Phe | Phenylalanine | UUU | UUC | | | | |
| G | Gly | Glycine | GGU | GGA | GGC | GGG | | |
| H | His | Histidine | CAU | CAC | | | | |
| I | Ile | Isoleucine | AUU | AUA | AUC | | | |
| K | Lys | Lysine | AAA | AAG | | | | |
| L | Leu | Leucine | UUA | CUU | UUG | CUC | CUA | CUG |
| M | Met | Methionine /START | AUG | | | | | |
| N | Asn | Asparagine | AAU | AAC | | | | |
| P | Pro | Proline | CCU | CCA | CCC | CCG | | |
| Q | Gln | Glutamine | CAA | CAG | UAA | UAG | | |
| R | Arg | Arginine | AGA | CGU | AGG | CGC | CGA | CGG |
| S | Ser | Serine | UCU | UCA | AGU | AGC | UCC | UCG |
| T | Thr | Threonine | ACU | ACA | ACC | ACG | | |
| V | Val | Valine | GUU | GUA | GUC | GUG | | |
| W | Trp | Tryptophan | UGG | | | | | |
| Y | Tyr | Tyrosine | UAU | UAC | | | | |
| | | STOP | UGA | ~~UAA~~ | ~~UAG~~ | | | |

Fig. 10

EXPRESSION OF MONOCLONAL ANTIBODIES IN CILIATE HOST CELLS

CROSS REFERENCE TO RELATED APPLICATIONS

The present application is a National Phase Application of International Application No. PCT/EP2011/053129, filed Mar. 2, 2011, which claims priority to Great Britain Patent Application No. 1003701.8, filed Mar. 5, 2010, which applications are incorporated herein fully by this reference.

SEQUENCE LISTING

Please direct entry of the attached "Sequence Listing" in the above-identified patent application. The enclosed txt copy of the Sequence Listing serves as both a paper copy of the sequence listing under 37 C.F.R. 1.821(c) and a computer readable form under 37 C.F.R. 1.821(e). The sequence listing attached hereto an in compliance with 37 C.F.R. 1.821(c) and (e) is identical to the paper copy of the Sequence Listing which was submitted in PCT Application No. PCT/EP2011/053129, filed on Sep. 9, 2011, and includes no new matter, as required by 37 C.F.R. 1.821(e), 1.821(f), 1.821(g), 1.825(b), or 1.825(d). Therefore, entry of the Sequence Listing is respectfully requested.

The present invention relates to a system for the heterologous expression of a monoclonal Antibody (mAb) in a ciliate host cell.

Today, the main indications of monoclonal antibodies for human therapy are cancer, autoimmune diseases and infectious diseases.

One mechanism of action is to interrupt the signalling pathways of growth factors which promote tumor-associated angiogenesis, as for example done by Avastin (Bevacizumab), which targets Vascular Endothelial Growth Factor (VEGF), thus starving the tumor. Other targets are, for example, Placental growth factor (PLGF). While for these purposes a high target affinity is mandative, which is mediated by the Complementary Determining Region (CDR) regions located on the variable regions of antibody light and heavy chains ($V_L$ and $V_H$), antibody effector functions as exerted by the Fc region are not crucial. For these purposes, antibody fragments devoid of an Fc region (like scFv, or Fabs) can be used Other mechanisms of action are the binding of cytokines, like TNFalpha (Humira), or the blocking of growth factor receptors, like erbB-2 (Erbitux), of viral surface antigens necessary for cell entry, like RSV F-Protein (Synagis), or of receptors responsible for blood clotting, like IIb/IIIa-receptors of RBC (ReoPro).

However, monoclonal antibodies can also be used for target cell-killing applications, e.g., for elimination of cancer cells or pathogens. While conjugated antibodies, i.e., artificial antibodies carrying a particular cytotoxin, have been developed for this purpose, unconjugated antibodies devoid of a particular cytotoxin can meet this goal as well by evoking respective immune responses. For these purposes, however, a functional Fc region is necessary, are provided in IgGs, particularly IgG1. Basically, four different mechanisms are known in this context:

The Fc region of target-cell bound antibodies can bind to Fc gamma receptors (FcγRs, particularly FcγRI, FcγRIIa and/or FcγRIII) on the surface of immune effector cells, and trigger FcγR-mediated killing of the target cells by immune effectors ("Antibody-Dependent Cellular Cytotoxicity", or ADCC);

The Fc region of target-cell bound antibodies can bind to soluble proteins of the complement system found in blood (e.g., Clq), and trigger complement mediated lysis of target cells ("Complement-Dependent Cytotoxicity", CDC);

Direct binding of the antibody to the target molecules can trigger cell death-inducing mechanisms, such as apoptosis (Antibody-Dependent Apoptosis), or can block the action of cell survival factors, such as growth factors;

Opsonisation of a target cell by antibody-mediated binding of macrophages or neutrophiles, and subsequent phagocytosis.

ADCC is a mechanism of cell-mediated immunity whereby an effector cell of the immune system actively lyses a target cell that has been bound by specific antibodies. It is one of the mechanisms through which antibodies, as part of the humoral immune response, can act to limit and contain infection. Classical ADCC-mediating effector cells are natural killer (NK) cells; but monocytes and eosinophils can also mediate ADCC. ADCC is part of the adaptive immune response due to its dependence on a prior antibody response.

Therapeutic antibodies which are used to elicit an ADCC in target cells need an Fc region in order to be recognized by Fc gamma receptors of the said effector cells. Examples for such antibodies are Herceptin, which recognizes erbB-2 and binds preferably to tumor cells overexpressing erbB-2, or Rituxan, which binds to the CD20 receptor in malignant B-Cells One other potential mechanism is to bring two or more different entities into close proximity, namely by using a bi- or higher specific antibody construct. This is for example useful to re-direct T cells against tumor cells, in cases the tumor cells can escape from T cell attack, e.g., by mutation, or loss, of their MHC class I entities, or by secreting messenger substances that suppress T cell activation. One approach is to combine two scFv antibodies, out of which one is directed against a T-cell-receptor (e.g., CD 3), while the other one is directed against a tumor cell antigen (e.g. EGFR).

Another approach is to connect (by means of a fusion molecule comprising two different complementary determining regions in both Fv chains, and a Fc-region), a tumor cell (e.g., by means of a Fv binding to EGFR or EpCAM), a T-cell (e.g., by means of another Fv binding to a T-cell receptor, like CD3) and an effector cell, such as a monocyte, a macrophage or a natural killer cell (by means of the Fc region which is detected by Fc gamma receptors on such effector cells). This approach brings together the anti-tumor effect of T killer cells, which induce tumor cell lysis and apoptosis, and of effector cells, which eliminate tumor cells by phagocytosis or apoptosis, while they release cytokines which further stimulate T cell activity.

Yet another approach is to design an Antibody, in which two different antigens can be recognized by one antigen binding site, both with high affinity Such antibodies may in future replace combination therapies with two different antibodies. Furthermore, such antibodies could also be used to combine different epitopes of the same antigen, especially of soluble antigens, to increase the binding avidity and in vivo potency Currently, antibodies or fragments or derivatives thereof for therapeutical use are expressed either in *E. coli* or mammalian cell lines, like CHO (chinese hamster ovary) cells. These systems do not allow to enhance ADCC or provide antibodies with multiple specifity, and have some other disadvantages.

Antibodies produced in *E. coli* come without a glycosylation or other post translational modifications, and have therefore limited capabilities related to ADCC. Furthermore, *E. coli* strains do not secrete proteins into the medium, so cells have to be lysed and antibodies need thorough purification. Another well-known problem is the incorrect folding of proteins which can lead to the formation of insoluble inclusion bodies. As a consequence, *E. coli* is only suitable for the production of Fab and scFv fragments, which have poor serum half life.

Eukaryotic expression systems also suffer from a number of drawbacks. Yeast expression systems tend to produce hyperglycosylated proteins rich in mannose, which often lead to unwanted immune reactions when the therapeutic antibody is administered to a patient. Baculovirus transfected insect cell systems cause problems due to hypoglycosylation, which negatively affects the effector function of therapeutic antibodies. Furthermore, the major disadvantage are the catalytitc properties of infectious baculovirus that narrows the window for full IgG production.

Mammalian and human cell lines, like CHO and Per.C6 cells, are difficult to culture and grow, and expensive to upscale. Additionally, these cells have high demands related to the culture medium. Moreover, mammalian and human cell lines bear the risk of infections with bacteria and viruses of human or animal origin.

OBJECT OF THE INVENTION

It is one object of the present invention to provide a system for the expression of antibodies, or fragments or derivatives thereof, which does not have the disadvantages set forth above.

It is one other object of the present invention to provide a system which allows the production of antibodies, or fragments or derivatives thereof, with increased ADCC, CDC, Antibody-Dependent Apoptosis or Antibody-Dependent Opsonisation.

It is one other object of the present invention to provide a system which allows the production of antibodies, or fragments or derivatives thereof, with multiple specifity.

It is one other object of the present invention to provide a system which allows the production of antibodies, or fragments or derivatives thereof, with an extended serum half life.

These objects are met with a system according to the independent claim. Dependent claims describe preferred embodiments, while other independent claims describe variants and/or alternatives.

SUMMARY OF THE INVENTION

According to the invention, a system for the heterologous expression of a monoclonal Antibody (mAb) or a fragment or derivative thereof, is provided, said system comprising
a) at least one ciliate host cell, and
b) incorporated, into said ciliate host cell, at least one heterologous nucleic acid molecule encoding for said monoclonal antibody, or a fragment or derivative thereof.

The term "heterologous expression", as used herein, shall refer to the protein expression of a gene, a nucleic acid or a cDNA, which is foreign to the organism in which the expression occurs.

As used herein, the term "nucleic acid molecule" is intended to indicate any single- or double stranded nucleic acid molecule comprising DNA (cDNA and/or genomic DNA), RNA (preferably mRNA), PNA, LNA and/or Morpholino. Preferably, said nucleic acid molecule comprises a cDNA encoding for a monoclonal antibody, or a fragment or derivative thereof.

The term "cDNA", as used herein, shall refer to a DNA molecule which encodes for a protein to be expressed, and is devoid of any non-encoding parts, like introns. In many cases, a cDNA has been directly synthesized from an RNA template using reverse transcriptase, and an oligo dT-primer. However, the term shall as well comprise synthetic genes and encoding DNAs otherwise obtained.

Nucleic acid sequences encoding for given monoclonal antibodies against given targets can be taken from literature. In European Patent EP0590058B1, for example, the amino acid sequences of the $V_L$ domain and the $V_H$ domain of the humanized monoclonal anti-Her-2/neu Antibody Herceptin (Trastuzumab) are disclosed. Other references describe even the amino acid sequence for full IgGs. With this information, the skilled person could design a cDNA encoding for such antibody, and use it for the purpose of the present invention.

Other resources are, for example, the public DrugBank database (http://www.drugbank.ca), which provides sequence information for most monoclonal antibodies, or fragments or derivatives thereof.

As used herein, the term "monoclonal Antibody (mAb)", shall refer to an antibody composition having a homogenous antibody population, i.e., a homogeneous population consisting of a whole immunoglubolin, or a fragment or derivative thereof. Particularly preferred, such antibody is selected from the group consisting of IgG, IgD, IgE, IgA and/or IgM, or a fragment or derivative thereof.

As used herein, the term "fragment" shall refer to fragments of such antibody retaining, in some cases, target binding capacities, e.g.
- a CDR (complementarity determining region)
- a hypervariable region,
- a variable domain (Fv)
- an IgG heavy chain (consisting of $V_H$, $C_H1$, hinge, $C_H2$ and $C_H3$ regions)
- an IgG light chain (consisting of $V_L$ and $C_L$ regions), and/or
- a Fab and/or F(ab)2.

As used herein, the term "derivative" shall refer to protein constructs being structurally different form, but still having some structural relationship to, the common antibody concept, e.g. scFv, as well as bi-, tri- or higher specific antibody constructs. All these items are explained below.

The term "host cell", as used herein, has two different meanings which may be understood according to the respective context. In the context of heterologous protein expression, the term "host cell" refers to a transgenic cell which is used as expression host. Said cell, or its progenitor, has thus been transfected with a suitable vector comprising the cDNA of the protein to be expressed.

As used herein, the term "ciliate host cell" shall refer to a cell from the phylum Ciliophora (formerly: Ciliata), e.g., protozoans characterized by the presence of hair-like organelles called cilia and a nuclear dimorphism.

As used herein, the term "incorporated" shall refer to the fact that the said nucleic acid has entered the host cell in such way that it is ready for protein expression. Such incorporation can have different types in ciliates, e.g. "episomal incorporation" (e.g. the nucleic acid molecule, like a plasmid, has not entered the cellular nucleus, but replicates, and is translated, in the cytoplasm), and "integrative incorporation" (e.g. the nucleic acid molecule has integrated into the cellular genome).

Ciliates have some surprising properties which make them suitable for use as expression hosts for monoclonal antibodies, or fragments or derivatives thereof. In contrast to E. coli, they can not only produce scFv and Fab, but also full scale immunoglobulins (IgG). Furthermore, the produced antibody can be secreted into the medium, so cell lysis and extraction from the cell pellet is not necessary.

Compared to mammalian cell lines, antibody expression is very cheap, as ciliates have little demands related to the culture medium, and can be cultured in liquid cultures.

Furthermore, the inventors have realized that for ciliates, unlike as for bacteria or higher eukaryotes, no specific viruses are known so far. This might be due to the nuclear dimorphism which is common to ciliates. Another reason for this might be the unusual codon usage and AT-rich genome in Ciliates. The inventors do thus assume that pathogenic viruses of higher organisms cannot amplify in most ciliates. The fact that, as known so far, ciliates are not susceptible for viruses, arises as a surprising advantage. This means that in production processes based on Ciliates, amplification or growth of adventitious viruses does not occur. This means, furthermore, that in case a protein is produced for therapeutic use, costly virus depletion procedures as necessary in industrial processes with human and animal cell cultures can be skipped.

Ciliate systems have, however, some other advantages with respect to the expression of monoclonal antibodies. These will be discussed in the following.

Despite the said advantages, ciliate expression systems are still relatively unknown, and the person skilled in the art, when being asked about potential heterologous protein expression systems, would rather think of E. coli, yeast, insect cell systems (baculovirus) and mammalian cell lines.

Methods for the transformation of ciliates, which can be used in the context of the present invention, comprise, among others, microinjection, electroporation and particle bombardment, and are, for example, described in Tondravi & Yao (1986), Gaertig & Gorovsky (1992) and Cassidy-Hanley et al (1997).

Methods for transformation and heterologous protein expression have been described for a few protists (WO 00/58483 and WO 00/46381). The generation of mitotically stable transformants of the ciliate Tetrahymena thermophile can be achieved after transfection either of the somatic macronucleus or the generative micronucleus by microinjection, electroporation or by particle bombardment.

Selection of the transformants can be performed using different selection markers like the neomycin resistance (Weide et al. 2006, BMC) and the integration of the heterologous genes by homologous DNA recombination, which results in stable thymidine-auxotrophic Tetrahymena cells (Weide et al. 2006, BMC). In addition, the use of blasticidin S (Weide et al. 2007, BMC) or paclitaxcel (WO 00/46381) resistance has also been considered.

Preferably, the encoding nucleic acid is codon optimized for a ciliate expression host. The term "codon optimized", as used herein, shall refer to a process in which the cDNA encoding the heterologous protein to be expressed is adapted to a host specific codon usage which derives from the universal genetic code scheme. Ciliates have an AT-rich genome, with Tetrahymena DNA consisting of approximately 75% AT (see FIG. 9). The codon usage differs from that in other organisms particularly in how often a codon is used to encode a given amino acid ("codon bias"). If the non-optimized cDNA encoding a heterologous protein uses codons which are rarely used in ciliates this might strongly affect the protein expression efficiency.

This means, in turn, that heterologous protein expression can improve dramatically when the codon frequency of the gene under study is matched to that of the ciliate expression system. Moreover, many ciliates, among them Tetrahymena, utilize non-canonical nucleotide codes with UAA and UAG tripletts encoding for glutamine, while in most other organisms these codons are used as stop codon which terminate translation. This may lead to the fact that foreign (non ciliate) genes carrying UAA and UAG tripletts as stop codon are not correctly expressed. For this purpose, before transforming the ciliate host cell, the cDNA encoding a heterologous protein should be code optimized in such way that UAA and UAG tripletts are amended into UAA. Code optimization can for example be accomplished by site directed mutagenesis, or by de novo cDNA synthesis.

In a preferred embodiment of the present invention, said monoclonal Antibody (mAb), or a fragment or derivative thereof, has an N-glycan structure which is essentially fucose-free. Proteins expressed in eukaryotic expression systems undergo a process of post-translational modification, which involves glycosylation. Eukaryotic expression systems which have been established today for the production of IgG and other monoclonal antibodies comprising an Fc region add N-glycans to the polypeptide chains. In IgG, the most important N-glycan is bound at Asn 297 of both $C_H2$ chains (see FIG. 1), which comprises, among others, N-acetyl-neuraminic acid (sialic acid), N-acetyl-glucosamine, galactose, mannose, and fucose residues. This applies, basically, for transgenic plant expression systems as well as for mammalian cell lines (see FIG. 2), insect cell lines etc. In all these cases, the N-glycan comprises at least one fucose residue which is bound either α-3-glycosidically or α-6-glycosidically to the N-acetyl-glucosamine residue bound to the Asn residue of the polypeptide chain.

In contrast thereto, ciliates produce an N-glycan structure which is significantly different from the glycoslation patterns produced by the above mentioned expression systems in that it does not contain fucose.

As used herein, the term "essentially fucose-free" means that the share of monoclonal antibodies, or fragments or derivatives thereof, carrying one or more fucose residues in one or more N-glycans, preferably in Asn 297 N-Glycans, does not exceed 10%, preferably 5%, more preferably 1%, and most preferably 0.1% of the total of monoclonal antibodies, or fragments or derivatives thereof, produced with the system according to the invention.

Furthermore, production of recombinant antibodies in human cell lines (PerC6) as wells as in common mammalian cell lines lead to glycosylation profiles that varies with culture conditions and over the course of the culture period. This reduced fidelity in antibody glycosylation pattern contributes to an diminished therapeutic efficiency and increases the risk of adverse effects (Jefferis 2005). Ciliates, in contrast, are able to secrete proteins with an highly reproducible biantennary oligomannose N-glycosylation structure (Banno et al. 1993). The like consistent glycosylation pattern lead to an uniform serum half life, reduced risk of adverse effects and likely enables an uniform and well manageable therapeutic effect.

In another preferred embodiment, said monoclonal Antibody (mAb), or a fragment or derivative thereof, has at least one effect selected from the group consisting of
increased Antibody-Dependent Cellular Cytotoxicity (ADCC)
increased Complement-Dependent Cytotoxicity (CDC),
increased Antibody-Dependent Apoptosis, and/or
increased Antibody-Dependent Opsonisation.

Recent studies have shown that monoclonal antibodies having a reduced amount of fucose in its glycosylation pattern exhibit much higher Antibody-Dependent Cellular Cytotoxicity (ADCC) activity as compared to fucosylated antibodies. Again, it is basically position Asn 297 where a lack of fucose residues leads to the increased ADCC. The mechanism behind the increased ADCC of a low/no-fucose Antibody seems to be mediated by an increased affinity of a so modified Fc region to FcγR, for example FcγIIIa (CD16), the major Fc receptor for ADCC in human immune effector cells (Shields et al, 2002).

Potential targets for therapeutic antibodies according to the present invention, eliciting an ADCC, are shown in the following table, which is not to be construed as limiting the scope of the present application (target abbreviations have been taken from standard literature):

TABLE 1

| target | potential indication | Antibody example |
|---|---|---|
| CD3 | graft versus host disease, kidney transplantation | OKT3 |
| CD4 | T-cell-lymphoma | HuMAX CD4 |
| CD5 | B/T cell antigen: MCL, CLL, CTCL, autoimmune | |
| CD19 | non hodgkin lymphoma, B cell malignancies and autoimmune diseases | AFM12, XmAb 5574; XmAb5871 |
| CD20 | non hodgkin lymphoma, rheumatoid arthritis, chronic lymphocytic leukemia, follicular non-Hodgkin's lymphoma, diffuse large B cell lymphoma | Rituxan, Bexxar, HuMAX CD20, Zevalin |
| CD22 | Non-Hodgkin-Lymphome | LymphoCide |
| CD30 | treatment of Hodgkins Lymphoma and anaplastic large cell lymphoma | XmAb2513; MDX060 (5F11) |
| CD33 | acute myeloid leukemia | Mylotarg |
| CD38 | multiple myeloma | HuMAX CD38 |
| CD40 | Alzheimer disease pathogenesis; B cell malignancies and autoimmune diseases | XmAb 5485 |
| CD52 | B-cell chronic lymphocytic leukaemia | Campath |
| CD70 | hematological malignancies | SGN70 and SGN75 |
| CEA | colorectal/lung/breast cancer | CEA-Scan |
| CTAA 16.88 | colorectal/breast/prostatic/lung/ovarian/pancreatic cancer | HumaSpect-Tc |
| GD2 | solid cancers | BIW-8137 |
| VEGF-R/FLT-1 | breast and colon cancer | BIW-8556 |
| GM2 | lung and brheumatoid arthritisin cancer | BIW-8962 |
| IL-5 receptor | Asthma | BIW-8405 |
| EGFR/Her2-neu | metastatic colorectal cancer and head and neck cancer, squamous cell carcinoma of the head and neck (SCCHN) | Erbitux, HuMAX EGFr |
| EpCAM | colon, breast and prostate cancer (solid tumors) | MT201, Panorex |
| ErbB2 | metastatic breast cancer overexpressing ErbB2 | Herceptin |
| FOLR1 | ovarian cancer | |
| PLAC1 | breast cancer, NSCL, ovarian cancers | GT468 |
| CLDN18.2 | gastric and pancreatic cancers | GC182 |
| Histone H1 | lung/uterine cancer gliomasarcoma | Cotara |
| CD317 | multiple myeloma | anti-HM1.24 |
| Muc1 | colon carcinoma | PankoMab |
| PSMA | prostatic cancer | ProstaScint |
| VEGF | metastatic colorectal cancer | Avastin |

It is important to understand that the skilled person has full access to manufacturing protocols and amino acid sequences of the above mentioned antibodies, and will thus be able to apply the teaching of the present invention to all of the said antibodies, e.g., in order to enhance the ADCC evoked by the latter.

US company Xencor has developed a modular suite of antibody components by engineering antibody Fc regions for select amino acid changes. In some cases, these Fcs have reportedly been shown to increase the ADCC more than 100-fold, resulting, among others, in ADCC killing even against cell lines expressing low levels of antigen and the reduction of doses of mAb while maintaining the same cytotoxic effect. However, the authors draw no causal relationship between their modifications, which seem to be based on a random mutation/selection process, and the resulting effects, i.e. increased ADCC. For this reason, the concept is not fully reproducible, and it is unknown whether or not it can be generalized to other Antibodies.

Japanese company BIOWA has developed a CHO (Chinese Hamster Ovary) cell line for the expression of mAbs with increased ADCC. In this cell line, the gene encoding for the α-1,6 Fucosyltransferase ("FUT8") enzyme has been knocked out. Thus, during post translational glycosylation, fucose residues cannot be added to the N-glycosylation site of the antibodies. It is claimed that mAbs thus produced show an enhanced ADCC activity. The method is described in EP1176195. A major drawback of this technique is that it does not ensure a 100% fucose free product. Defucosylation is highly dependent on a potentially remaining enzyme activity of the α-1,6 fucosyltransferase, and thus subject to significant variance, particularly on a batch-to-batch comparison. Furthermore, the system is only available in CHO cells (so-called FUT8 knock out CHO), which are suboptimal expression hosts for some mAb expression applications.

US company Glycart has developed cell lines for the production of mAbs which carry a heterologous gene for encoding the oligosaccharide-modifying enzyme beta (1,4)-N-acetylglucosaminyltransferase III (GnT III). When these cells are later on transfected with a DNA encoding for a mAb, they will produce mAbs which first undergo a normal glycosylation process, including the incorporation of fucose residues. In a second step, the fucose residues are then cleaved by means of the GnT III enzyme. The resulting proteins are thus more or less unfucosylated and exhibit an increased ADCC. Again, this technique does not ensure a 100% fucose free product. Defucosylation is highly dependent on the activity of said GnT III enzyme, and thus subject to significant variance, particularly on a batch-to-batch comparison.

US company Eureka Therapeutics is advertising that they have developed a method to enhance ADCC in therapeutic antibodies which they have named MAGE ("Magnified ADCC through Glycosylation Engineering"). However, technical details of the method have not been revealed.

Surprisingly the inventors of the present invention have found in their experiments, that ciliates produce antibodies that can induce ADCC, although the N-glycan structure is different to typical antibodies expressed in mammalian cells. Subsequently, the inventors of the present application found in their experiments that ciliates produce antibodies with an N-glycan structure in the Fc-region, which does not contain fucose. This can be an explanation for the increased ADCC effector function, compared to antibodies expressed in mammalian cells.

The system according to the invention thus provides an economical, simple and reliable method for the production of monoclonal antibodies, or fragments or derivatives thereof, which have a drastically increased ADCC and thus a highly enhanced therapeutic potential.

It is important to mention that yeast-based expressions systems (e.g., *Saccharomyces* sp., or *Pichia* sp.) also produce unfucosylated N-glycans (see FIG. 2) rich in mannose. While these expression systems are subject of intensive research, particularly for the production of antibodies, or fragments or derivatives thereof (Wei et al, 2008), it seems that the major focus of research is directed to modifying the glycosylation pattern of a yeast-based expression system in such way that it is similar to human glycosylation patterns (Gerngross, 2004). This, in turn, would not only be useful for antibodies, or fragments and derivatives thereof, but also for other biopharmaceuticals expressed.

Today, no reports are available which indicate that antibodies, or fragments or derivatives thereof, produced in yeast strains have an increased ADCC, or CDC, or Antibody-Dependent Apoptosis, nor that the lack of fucosylation has any other particular effect. This again indicates that a lack of fucosylation alone does not automatically mean an increased ADCC—a fact well known by the skilled person.

Furthermore, it seems that therapeutical antibodies, or derivatives or fragments thereof, produced with the system according to the invention, also have an increased CDC.

Furthermore, it seems that therapeutical antibodies, or derivatives or fragments thereof, produced with the system according to the invention, also have increased Antibody-Dependent Apoptotic effects.

Furthermore, it seems that therapeutical antibodies, or derivatives or fragments thereof, produced with the system according to the invention, also have increased Antibody-Dependent Opsonization effects.

In a particularly preferred embodiment, it is provided that additional N-glycosylation sites are introduced into the antibody, or fragment or derivative thereof, which is to be expressed. This can be done by introducing, for example by site-directed mutagenesis, or by deliberate exchange of amino acid residues, additional N-glycosylation motifs, i.e., tripeptide sequences Asn-X-Ser or Asn-X-Thr, where X can be any amino acid, although Pro and Asp are rarely found. If for example the antibody, or fragment or derivative thereof, has, somewhere in its chain, the motif "Gly-X-Ser", one could substitute "Gly" by "Asn", on order to create an additional N-glycosylation site. It is of course necessary to make sure that the said substitution does not affect important properties of the protein, like target affinity, binding by Fc gamma receptors (FcγRs) or the like.

However, the exceptional N-glycoslation pattern, does, at first sight, rule out the use of *Tetrahymena thermophile* as expression system for antibodies for therapeutical use, as the skilled person would consider that such abnormal glycosylation pattern affects immunocompatibility of the antibodies thus produced. The inventors have, however, shown that these presumptions are not correct.

Furthermore, ciliate expression systems have other advantages in comparison to other protein expression systems, like mammalian cell lines, which are discussed below.

In yet another preferred embodiment, said monoclonal Antibody (mAb), or a fragment or derivative thereof, has an extended serum half life.

Serum half life is an important issue in monoclonal antibodies used for therapeutic purposes, as an extension of the former may help to reduce the dosage and/or the administration frequency. As monoclonal antibodies can not be administered orally, this would help to improve the patient compliance, while reducing costs because of lower doses and minimizing risks related to the way of administration.

A major pathway of removing dissolved proteins from the serum is the asialoglycoprotein receptor-mediated clearance in the liver. Usually, mammalian proteins are N-glycosylated with bifurcated N-glycans having two or more terminal sialic acid residues (N-acetyl-neuraminic acid), which are backed up by beta-galactose residues (see FIG. 2). This applies both for a subject's intrinsic proteins as well as for proteins heterologous expressed, e.g., in a mammalian cell line, and administered to said subject.

During the protein life span, the terminal sialic acid residues are gradually removed from the glycan chain because of ubiquitous neuraminidases, until the galactose residues are exposed. These are then recognized by asialoglycoprotein receptors, which are lectins abundant in the liver binding galactose residues of many desialylated plasma proteins. After being recognized, the said proteins are subject to endocytosis, and will then be degraded in the liver.

As shown above, proteins heterologous expressed in ciliates have neither terminal sialic acid residues, which could be removed by free floating neuraminidases, nor galactose residues, which could serve as a target for asialoglycoprotein receptors. For this reason, monoclonal antibodies, or fragments or derivatives thereof, which have been heterologous expressed in ciliates, are not subject to the asialoglycoprotein receptor-mediated clearance, and do therefore have an enhanced serum half life. The ciliate—expression approach has some significant advantages over other approaches to extend antibody serum half life, which all involve more or less dramatic modifications of the basic antibody concept, the consequences of which for immunogenicity and the like are difficult to predict. These approaches are discussed in the following.

US company Domantis tries to extend serum half life by using an anti-albumin domain bound to antibodies, while Genentech Inc. has developed an approach in which the galactose content in $CH_2$—N-glycans is increased. PDL BioPharma Inc. developed an approach in which some amino acid residues in the Fc-region are substituted by others, thus leading to an extension of serum half life. Furthermore, the concept of PEGylation is well known to the skilled in order to extend serum half life of a protein.

In yet another preferred embodiment of the invention, the said system further comprises c) a promoter operably linked to said nucleic acid molecule, and/or d) a signal sequence operably linked to said nucleic acid molecule, which signal sequence accounts for the secretion of the monoclonal antibody, or the fragment thereof, encoded by the said nucleic acid molecule, into the extracellular medium.

The term "operably linked" as used herein, means that a nucleotide sequence, which can encode a gene product, is linked to a promoter and/or a signal sequence in such way that the promoter regulates expression of the gene product under appropriate conditions.

The term "promoter", as used herein, shall refer to a regulatory region of DNA generally located upstream (towards the 5' region of the sense strand) of a gene or a cDNA, that contains essential genetic elements which allow or even enhance transcription of the gene, or the cDNA.

The term "signal sequence", as used herein, shall refer to a nucleic acid sequence which encodes for an oligopeptide ("signal peptide" or "transit peptide") which directs the transport of a protein to certain organelles such as the nucleus, mitochondrial matrix, endoplasmic reticulum, chloroplast, apoplast and peroxisome. Almost all proteins that are transported to the endoplasmatic reticulum have a sequence consisting of 5-10 hydrophobic amino acids at the N-terminus. Those signal peptides are cleaved from the protein by a signal peptidase after the cotranslational insertion of the protein into the luman of the ER. Most proteins are then transported via Golgi apparatus downstream on the secretory pathway.

Promoters suitable for antibody expression in ciliates are, for example, disclosed in WO2007006812A1 which is also registered for the applicant of the present invention, the content of which shall be incorporated herewith by reference. Therein, a heat-inducible promoter and a metallothionein-promoter are disclosed which can also be used for the purposes of the present invention.

Suitable signal sequences are, for example, disclosed in WO03078566A1 which is also registered for the applicant of the present invention, the content of which shall be incorporated herewith by reference. Therein, two signal peptides particularly preferred in the context of the present invention are disclosed, namely the endogenous signal peptide of the antibody heavy and light chain, and the ciliate lipase signal peptide.

Furthermore, a vector for the transfection of a ciliate host cell is provided, said vector comprising at least one nucleic acid molecule encoding for a monoclonal Antibody (mAb), or a fragment or derivative thereof.

The term "vector", as used herein, refers to a molecular vehicle used to transfer foreign genetic material into another cell. The vector itself is generally a DNA sequence that consists of an insert (sequence of interest) and a larger sequence that serves as the "backbone" of the vector. The purpose of a vector to transfer genetic information to another cell is typically to isolate, multiply, or express the insert in the target cell.

The term "plasmid", as used herein, refers to plasmid vectors, i.e., circular DNA sequences that are capable of autonomous replication within a suitable host due to an origin of replication ("ORI"). Furthermore, a plasmid may comprise a selectable marker to indicate the success of the transformation or other procedures meant to introduce foreign DNA into a cell and a multiple cloning site which includes multiple restriction enzyme consensus sites to enable the insertion of an insert. Plasmid vectors called cloning or donor vectors are used to ease the cloning and to amplify a sequence of interest. Plasmid vectors called expression or acceptor vectors are specifically for the expression of a gene of interest in a defined target cell. Those plasmid vectors generally show an expression cassette, consisting of a promoter, the transgene and a terminator sequence. Expression plasmids can be shuttle plasmids containing elements that enable the propagation and selection in different host cells.

In yet another embodiment of the present invention, a system for the heterologous expression of a monoclonal Antibody (mAb) or a fragment or derivative thereof is provided, said system comprising a ciliate host cell which has been obtained by conjugation of at least two ciliate host cells according to the invention.

All ciliates exhibit a nuclear dimorphism with two structurally and functionally different types of nuclei. The large, somatic macronucleus (MAC) is actively expressed during vegetative multiplication. The MAC contains 45 chromosome copies and divides by amitosis. The small, diploid micronucleus (MIC) is the germline and contains 5 pairs of chromosomes. The MIC stores the genetic information for the sexual progeny. During the vegetative phase the MIC is divides mitotically. The life cycle of ciliates consists of alternating haplophases and diplophases with reference to the germline. The cell reproduction is exclusively asexual and occurs only in the diplophase.

The above approach utilizes a unique feature of ciliate host cells, namely that they can exchange genetic matter by conjugation. Under certain conditions ciliates will enter a conjugation cycle, the sexual stage of the life cycle. In *Tetrahymena*, for example, cells can be induced to conjugate by mixing cells belonging to at least two out of seven different mating types, and moderately starving them. During this stage, two cells pair to exchange haploid gametic nuclei. The nuclear events of conjugation normally include meiosis, gamete nucleus formation, fertilization, and nuclear differentiation. Conjugation includes the only—and very brief—haploid stage of the ciliate life cycle; it follows meiosis and quickly ends at fertilization. This process is conserved among the majority of ciliates.

Figure 6:
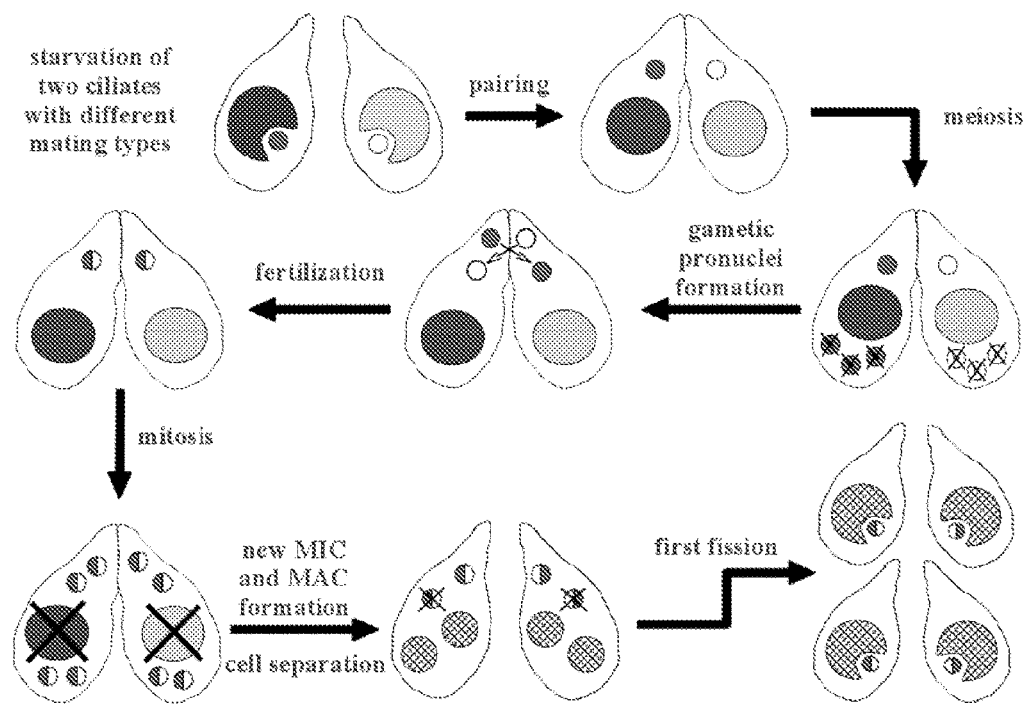

The claimed approach utilizes the unique feature of ciliate host cells, namely the exchange genetic material during conjugation. The main stations of the conjugation process are shown in FIG. 6.

At the start of conjugation, micronuclei in paired cells undergo meiosis, generating four haploid pronuclei. Three of these pronuclei are destroyed, while the remaining one divides to form two gametic nuclei: a "migratory" pronucleus and a "stationary" pronucleus. Migratory pronuclei are exchanged through a temporary junction of the two cells; these then fuse with a stationary pronucleus to form a zygotic nucleus in each cell.

The zygotic nucleus divides twice to form four genetically identical nuclei, whereas the old macronucleus is degraded. Two of the four zygotic clones (anterior products) develop into new macronuclei, which undergo a wide array of genome rearrangements, including chromosome breakage, programmed DNA elimination, and telomere addition. In *Tetrahymena* these processes generate approximately 300 individual macronuclear chromosomes. Each chromosome is then amplified to 45 copies, completing development of the macronuclear genome.

One of the two remaining zygotic clones is degraded; the other, the new micronucleus, divides mitotically during the first asexual reproductive cycle. The daughter cells each receive one micronucleus and one macronucleus in this division, yielding the normal complement of nuclei found in vegetatively growing ciliate cells.

The principle of conjugation is absent in prokaryotic expression systems as well as in most other eukaryotic expression systems, like yeasts, insect cell systems (baculovirus), mammalian expression systems, like CHO cells, or transgenic plants or mammals. Ciliate host cell which are used for recombinant expression of bi- or higher specific antibodies using conjugating of two different antibody expressing host cells according to the above system need to meet some requirements:
a) the at least two ciliate cells need to be from different mating types
b) the at least two ciliate cells need to have incorporated a nucleic acid molecule, encoding for a monoclonal Antibody (mAb), or a fragment or derivative thereof, into its micronucleus.

By conjugating the cells, a cell can be produced which carries a combination of both nucleic acid molecules, and can thus produce a new monoclonal antibody or antibody construct, or fragments or derivatives thereof, composed of the combination of the two parent antibodies, constituting e.g. both antigen specifities.

The following table gives an overview over some potential constellations which are within the scope of said invention. Indicated are the possible resulting combination antibodies, fragments or derivatives thereof after the conjugation of two host cells each carries an nucleic acid encoding for a monoclonal antibody. The list is not to be construed as limiting the scope of the present invention.

TABLE 2

| cell 1 prior to conjugation | cell 2 prior to conjugation | after conjugation |
| --- | --- | --- |
| whole IgG A | whole IgG B | bispecific full IgG F(ab)$_2$ A + Fc B |
| heavy chain ($V_H$) + light chain ($V_L$) | heavy chain ($V_H$) + light chain ($V_L$) | whole IgG |
| heavy chain ($V_H$) + light chain ($V_L$) against target 1 | heavy chain ($V_H$) + light chain ($V_L$) against target 2 | quadroma (bispecific) |
| scFv specific against target 1 (e.g. EGFR) | scFv specific against target 2 (e.g. CD3) | diabody or tandem scFv |
| heavy chain ($V_H$) + light chain ($V_L$) against tumor cell target (e.g. EGFR) | heavy chain ($V_H$) + light chain ($V_L$) against T-cell receptor (e.g. CD3) | trispecific antibody binding tumor cell, T cell and effector cell |
| Fab from antibody A | Fab from antibody B | bispecific F(ab)2 |
| Fab from antibody A | Fab from antibody B | F(ab)2 with bispecific antigen binding site ($V_L$(A) + $V_H$(B)) |
| bispecific whole IgG (A + B) | full IgG C | trispecific whole IgG: F(ab)2 A + B + Fc from C |

In another embodiment of the invention a ciliate host cell transfected with at least one vector according to the invention, or obtained by conjugation of at least two ciliate host cells according to the invention, is provided.

Furthermore, according to another embodiment of the present invention, a library comprising at least two ciliate host cells according to the invention, or at least two systems according to the invention, are provided wherein each host cell has incorporated at least one heterologous nucleic acid molecule encoding for an antibody, or fragment or derivative thereof, preferably in form of a vector, and wherein at least two ciliates are selected in such way that they can conjugate with one another.

Such library could, for example, comprise stable transfected ciliate host cells which each carry a nucleic acid molecule encoding for an antibody or fragment or derivate thereof (see below) specific against a given target (see, e.g. Tables 1 and 3). For each nucleic acid should encode for a given antibody or fragment or derivate thereof, host cells of at least two, preferably more, different mating types should be available. In case a bispecific antibody construct is to be built, two host cells can be selected from the library which carry the nucleic acid molecules for the two antibody or fragment or derivative thereof needed for the said construct. The said host cells should be from different mating types in order to conjugate them.

In a preferred embodiment of the system according to the invention, or a ciliate host cell according to the invention, the said ciliate is a member of the family Tetrahymenidae.

In a particularly preferred embodiment, the said transgenic ciliate is *Tetrahymena* sp. (particularly *Tetrahymena thermophila*). *Tetrahymena* is a nonpathogenic unicellular eukaryotic microorganism which has been established in a few laboratories as an expression host. It features a number of advantages which make it suitable for heterologous protein expression. *Tetrahymena* is a broadly examined model organism, and, in over 50 years of basic research, no viruses or endoparasites were observed. Examinations with indicator cell lines revealed no endogenous infectious agents like viruses or *mycoplasm*, which can infect higher animals.

First of all, the above considerations as related to codon usage in ciliates apply for *Tetrahymena* as well. Furthermore, high copy number plasmids are available for *Tetrahymena*, containing an origin of replication (ori) from a minichromosomal rDNA. This minichromosomal rDNA is present in up to 9.000 copies per cell. Beyond that stable integration can take place into the macronuclear DNA, in which all genes are present in 45-fold copy number. The high gene dose is the ideal precondition for an efficient protein biosynthesis and thus for a high productivity. In contrast to bacteria, ciliates of the genus *Tetrahymena* secrete biologically proteins very efficiently to the supernatant.

*Tetrahymena* is able to attach posttranslational modifications to proteins, like disulfide bridges, GPI anchor, phosphorylation, acetylation and glycosylation, which are more similar to those in mammalian cells than those detected in yeast or in other eukaryotic expression systems.

Unlike mammalian cells, *Tetrahymena* combines the ease of growth with short generation times (1.5-3 h), and cost reduction, as chemically defined media can be used and no need for peptides or serum components, like growth factors, exists.

Batch, fed-batch and continuous fermentation of *Tetrahymena* with cell densities up to $2 \times 10^7$ cells/ml and dry weights of up to 80 g/L are established, and production enlargements (upscaling) up to 1000 L could be demonstrated without any problem. In feasibility studies with reporter proteins space-time yields of 50-90 µg/cell a day could already be achieved. First experiments with homologous expression resulted in a yield of over 200 mg/L a day for secreted proteins. *Tetrahymena* can be fermented in conventional production facilities for microbiological expression systems (bacteria or yeasts). This means that no costly modifications in existing production plants or a new building of the production facilities are necessary.

In another preferred embodiment of the present invention, a monoclonal Antibody (mAb), or a fragment or derivative thereof is provided, said Antibody or fragment being produced with a system according to the invention, with a ciliate host cell according to the invention and/or with a process according to the invention.

Preferably, the monoclonal antibody, fragment or derivative according to the invention binds to at least one of the targets set forth in Table 1 (ADCC) or 3 (non ADCC)

Targets which are not involved in ADCC are listed in the following table, which is exemplary only and not to be construed as limiting the scope of the present invention.

TABLE 3

| target | indication | Antibody example |
| --- | --- | --- |
| TNF-α | rheumatoid arthritis, psoriasis, Morbus Bechterew, Morbus Crohn | Adalimumab, Golimumab, Infliximab |
| CD25 | prophylaxis of tissue rejection after kidney transplantation | Basiliximab, Daclizumab |
| CD3 | treatment of tissue rejection after organ transplantation | Muromonab-CD3 (murine) |
| CD49d (α4-Integrin) | multiple sclerosis | Natalizumab |
| interleukin 6 receptor | rheumatoid arthritis | Tocilizumab |
| Interleukin 12/23 | plaque-psoriasis | Ustekinumab |
| RSV surface antigen | prophylaxis of RSV in newborn | Motavizumab Palivizumab |
| VEGF-A | wet macular degeneration | Lucentis |
| CD11a-antigen | psoriasis | Efalizumab |
| Immunglobulin E | asthma bronchiale | Omalizumab |

Again, it is important to understand that the skilled person has full access to manufacturing protocols and amino acid sequences of the above mentioned antibodies, and will thus be able to apply the teaching of the present invention to the said antibodies, e.g., in order to enhance the serum half-life of the latter.

Furthermore, the monoclonal antibody, fragment or derivative according to the invention, is selected from the group consisting of
  murine, chimeric, humanized and/or human mAb,
  IgG, scFv, Fab and/or F(ab)$_2$,
  modified antibody format Methods for the production and/or selection of chimeric, humanized and/or human mAbs are known in the art. For example, U.S. Pat. No. 6,331,415 by Genentech describes the production of chimeric antibodies, while U.S. Pat. No. 6,548,640 by Medical Research Council describes CDR grafting techniques and U.S. Pat. No. 5,859,205 by Celltech describes the production of humanized antibodies. In vitro antibody libraries are, among others, disclosed in U.S. Pat. No. 6,300,064 by MorphoSys and U.S. Pat. No. 6,248,516 by MRC/Scripps/Stratagene. Phage Display techniques are for example disclosed in U.S. Pat. No. 5,223,409 by Dyax. Transgenic mammal platforms are for example described in US200302048621 by TaconicArtemis.

IgG, scFv, Fab and/or F(ab)$_2$ are antibody formats well known to the skilled person. Related enabling techniques are available from the respective textbooks.

As used herein, the term "Fab" relates to an IgG fragment comprising the antigen binding region, said fragment being composed of one constant and one variable domain from each heavy and light chain of the antibody As used herein, the term "F(ab)$_2$" relates to an IgG fragment consisting of two Fab fragments connected to one another by disulfide bonds.

As used herein, the term "scFv" relates to a single-chain variable fragment being a fusion of the variable regions of the heavy and light chains of immunoglobulins, linked together with a short linker, usually serine (S) or glycine (G). This chimeric molecule retains the specificity of the original immunoglobulin, despite removal of the constant regions and the introduction of a linker peptide.

Modified antibody formats are for example bi- or trispecific antibody constructs, as for example given in Table 2, antibody-based fusion proteins, antibody-drug conjugates, immunotoxins and the like. Some of these formats are listed in the following table, which is not to be construed as limiting the scope of the present invention.

TABLE 4

| company | format |
| --- | --- |
| Affimed | scFv-Diabody-scFv |
| Unilever | Camelid Antibodies |
| Ablynx | camelid VHH |
| Domantis | variable regions of heavy ($V_H$) or light ($V_L$) chain |
| Scancell | tumor epitopes on a IgG structure with unchanged FC domain |
| Hybritech | trifunctional antibodies |
| Trion Pharma | trifunctional IgG |
| Affitech | antibodies with T-cell epitopes between β-strands of constant domains, and new V-regions specific for antigen presenting cells |
| Affitech | antibody fragments that can cross link antigen and antibody effector molecules |
| Vaccibody AS | bivalent homodimers, each chain consisting of scFv targeting unit specific for antigen presenting cells |
| Planet Biotechnology | IgA (two IgG structures joined by a J chain and a secretory component), expressed in a plant host, secretory component replaced by a protection protein |
| Trubion | variable regions of heavy ($V_H$) and light ($V_L$) chain + Fc |
| Haptogen | homodimeric heavy chain complex found in immunized nurse sharks, lacking light chains |
| AdAlta | recombinant shark antibody domain library |
| Xencor | altered Fc region to enhance affinity for Fc gamma receptors, thus enhancing ADCC |
| Arana | new world primate framework + non-new world primate CDR |
| City of Hope | "minibody" |
| Seattle Genetics | antibody-drug conjugate technology with enzyme-cleavable linkers |

In other preferred embodiments, the monoclonal antibody, fragment or derivative according to the invention, has at least one feature selected from the group consisting of
  increased ADCC, CDC, and/or Antibody-Dependent Apoptosis,
  extended serum half life, and/or
  bi, tri- or multispecifity.

As used herein, the terms "increased ADCC", "increased CDC", "increased Antibody-Dependent Apoptosis", increased Antibody-Dependent Opsonization" and "extended serum half life" relate to a comparison with antibodies that have been produced with conventional Antibody expression systems, e.g., mammalian cells or E. coli. ADCC, CDC, Antibody-Dependent Apoptosis and serum half life can be measured with assays commercially available.

The terms "bi-", "tri-" or "multispecifity" refer to antibodies, fragments or derivatives thereof which have at least two domains exhibiting affinity against at least two different epitopes, preferably of at least two different targets. Some examples for such antibodies, fragments or derivatives are given in Table 2 and FIG. 4.

The purpose of such antibodies, fragments or derivatives thereof is to bring two or more different entities into close contact, namely by using a bi- or higher specific antibody construct. This is for example useful to re-direct T cells against tumor cells, in cases the tumor cells can escape from T cell attack, e.g., by mutation, or loss, of their MHC class I entities, or by secreting messenger substances that suppress T cell activation. One approach is to combine two scFv antibodies, out of which one is directed against a T-cell-receptor (e.g., CD 3), while the other one is directed against a tumor cell antigen (e.g. EGFR).

Another approach is to connect, by means of two different complementary determining regions in both Fv chains, and by the Fc-region, a tumor cell (e.g., by means of a Fv binding to EGFR), a T-cell (e.g., by means of another Fv binding to a T-cell receptor, like CD3) and an effector cell, such as a monocyte, a macrophage or a natural killer cell (by means of the Fc region which is detected by Fc gamma receptors on such effector cells). This approach brings together the anti-tumor effect of T killer cells, which induce tumor cell lysis and apoptosis, and of effector cells, which eliminate tumor cells by phagocytosis or apoptosis, while they release cytokines which further stimulate T cell activity.

The following table gives an overview of some exemplary targets in bispecific antibodies (first & second column) and trispecific antibodies (all three columns), but is not to be construed as limiting the scope of the present invention. Other suitable target epitopes are listed in Table 1.

TABLE 6

| Effector cell epitope | Target cell epitope | T cell activating epitope |
| --- | --- | --- |
| FcγRI | EGFR | CD3 |
| FcγRIIa | EpCAM | CD64 |
| FcγRIII | CD20 | CD16 |
| FcγRIII | CEA | CD89 |
| FcγRIII | CD19 | CD89 |

Some features of bispecific antibodies, including potential formats as well as targets, are discussed in Kufer et. al (2004), while features of trispecific antibodies, including potential formats as well as targets, are for example discussed in Ruf and Lindhofer (2001).

Furthermore, a process for the production of at least one monoclonal Antibody (mAb), or a fragment or derivative thereof, in a ciliate host cell, is provided, said process comprising the steps of
a) transfecting at least one ciliate host cell with at least one nucleic acid molecule encoding for said monoclonal antibody, or a fragment or derivative thereof, or, preferably, with at least one vector according to the invention, and
b) culturing the host cell under conditions which allow expression of a protein.

In another preferred embodiment of the present invention, a process for the production of at least one monoclonal Antibody (mAb), or a fragment or derivative thereof, in a ciliate host cell, is provided, said process comprising the steps of
c) transfecting at least two different ciliate host cells with at least one nucleic acid molecule encoding for an antibody, or a fragment or derivative thereof, or, preferably, with at least one vector according to the invention,
d) conjugating the said two ciliate host cells, or offspring thereof, in order to obtain at least one ciliate cell carrying at least two different nucleic acid molecules encoding for at least two different antibodies, or fragments or derivatives thereof, and
e) culturing the ciliate cell thus produced under conditions which allow expression of a protein.

Furthermore, a process for the production of a pharmaceutical composition is provided, said process comprising the steps of
a) expressing an antibody, or a fragment or derivative thereof protein according to the invention in a ciliate expression system according to the invention, and
b) isolating and/or purifying the protein thus obtained.

Furthermore, a pharmaceutical composition is provided, said composition comprising an Antibody, or a fragment or derivative thereof, according to the invention, and/or produced with a method according to the invention.

Disclaimer

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

BRIEF DESCRIPTION OF THE EXAMPLES AND DRAWINGS

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

EXAMPLES

1. Construction of Expression Vectors

Figure 5:
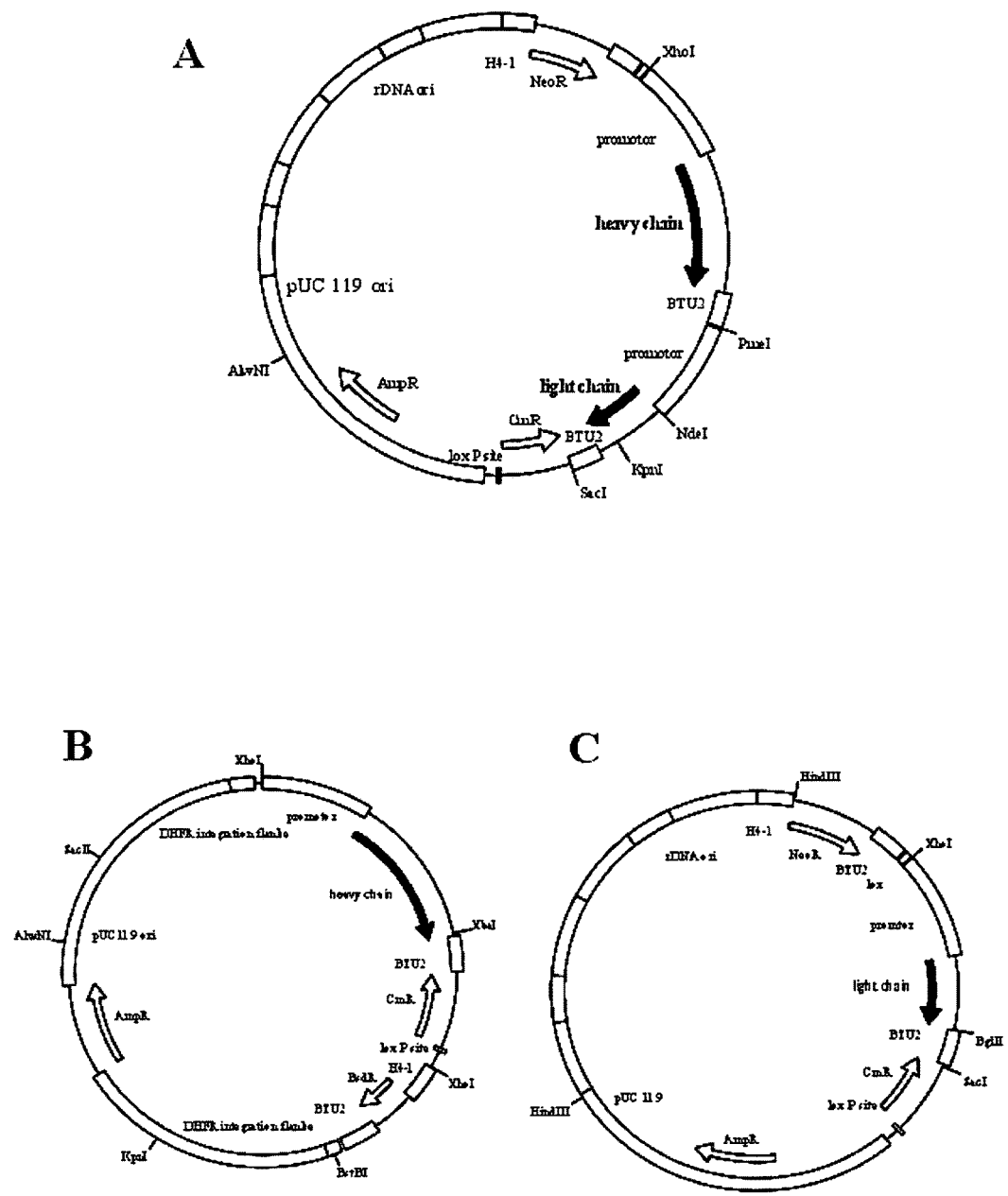

The synthetic genes for the heavy and light chain of the antibody Gk1.5 (see SEQ ID NOs 1 and 2) were cloned into the donor vector. The expression cassettes from all donor vectors were transferred into the acceptor vector (see FIG. 5) using a Cre dependent recombinase system.

2. Cultivation of Wildtype *Tetrahymena* and Transformation of Expression Plasmids Wildtype *Tetrahymena thermophila* strains (e.g. B 1868/4, B 1868/7 and B 2068/1) were cultivated in skimmed milk medium, in SPP or in chemically defined medium. The transformation of the *T. thermophila* cells was performed as previously described in Cassidy-Hanley et al. 1997.

3. Detection of Antibody Gk1.5

Transformed *Tetrahymena* cells were cultivated in SPP medium under selection pressure at 30° C. in a shaker at 80 rpm. Target gene expression was induced by heat shock at 41° C. (HSP-P) or by addition of 20 nM $Cd^{2+}$ (MTT1-P) of logarithmically growing cultures.

Figure 8:
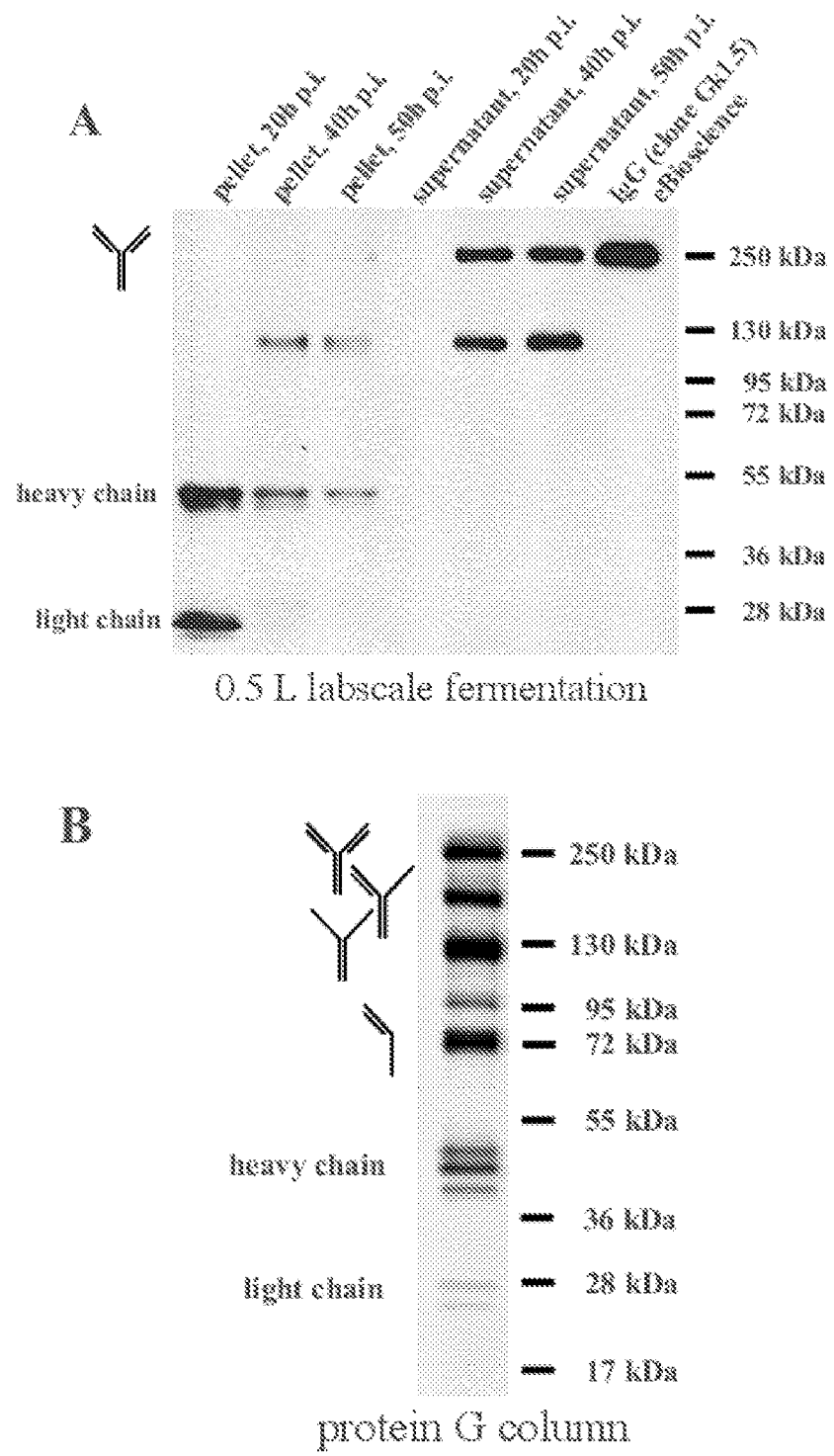

Aliquots of the culture were harvested 24 h after induction of target gene expression. Afterwards cells and cell free supernatant was gained, respectively. The cells were solubilized in ice cold RIPA-buffer (5000 cells/μl in 150 mM NaCl, 10 mM TrisHCl, 5 mM EDTA, 0.1% SDS, 0.1% DOC, 1% Triton X100, 2.5 μg/ml E64, pH 7.4) and incubated for 15 minutes in a sonicator. SDS-PAGE and Western blot analysis were done according to the art. Briefly, aliquots of either disrupted cells (i.e. 10 000 cells) or cell free supernatant were added to Laemmli sample buffer (125 mM Tris HCl pH 6.8, 10% Glycerol, 4% SDS) and separated using 8-16% SDS-PAGE. The proteins were transferred to nitrocellulose membranes and blocked in PBS containing 0.05% Tween 20 and 5% bovine serum albumin (PBS/TBSA). The expression of recombinant heavy and light chain of the antibody in transformed Ciliates was detected by an Hrp conjugated anti-rat-whole IgG-antibody. After washing the blots were developed by chemoluminescence using Super Signal West Pico Chemoluminescent Substrate (Perbio, Fischer Scientific) in combination with conventional X-ray film development. FIG. 8 shows Western blots of cell lysates and supernatants of transformed cells at different time points after the induction of target gene expression.

4. Production of Antibody Gk1.5

For fermentations a Sixforce multifermenter (0.5 Liter) equipped with standard marine impellers were used. Stirrer speed was limited to 900 rpm; pO2 was set to 25% and pH was set to 7.0, respectively. Fermentations were carried out in standard medium.

FIGURES

FIG. 1 shows a schematic representation of an immunoglobulin G (IgG). An IgG is composed of two identical light chains (each composed of two domains, $V_L$ and $V_H$) and two identical heavy chains (each composed of four domains, $V_H$, $C_H1$, $C_H2$ and $C_H3$). Antigen binding surface is formed by the variable domains of heavy and light chains and the effector function, such as complement activation and binding of cytotoxic cells is mediated by the Vc region of the antibody.

Figure 2A:
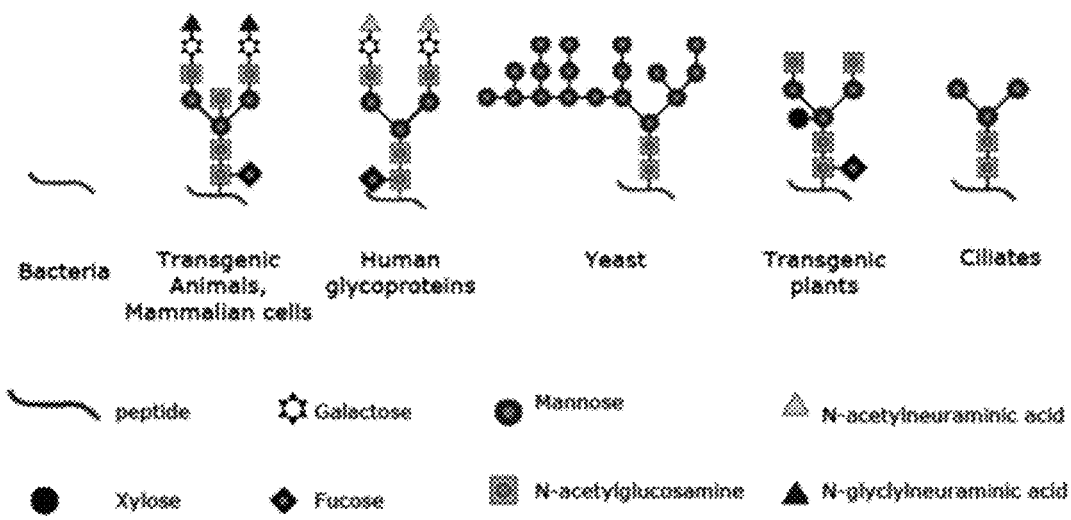
Figure 2B:
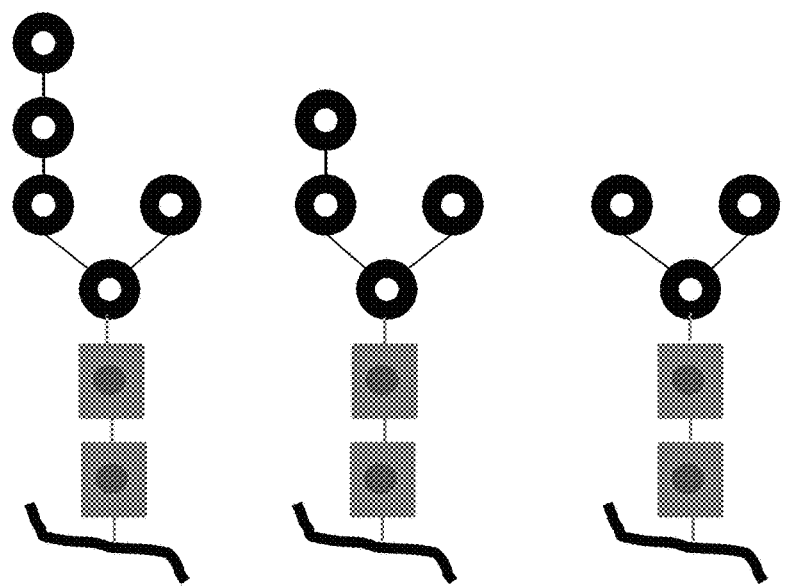

FIGS. 2A and 2B show an overview of N-glycan structures of different taxa. Generally, the term "N-glycosylation" refers to glycosylation of the amino acid residue asparagine (N). Here, an oligosaccharide chain is attached by oligosaccharyltransferase to those asparagine residues which occur in the tripeptide sequences Asn-X-Ser or Asn-X-Thr, where X can be any amino acid except Pro. It is obvious that, while prokaryotes have no N-glycosylation at all, ciliates feature N-glycan structures which are devoid of the fucose side chain and lack, furthermore, terminal sialic acid residues (n-acetyl-neuraminic acid) backed up by beta-galactose residues. FIG. 2*b* shows potential variations in the said pattern in some ciliate species.

Figure 3:
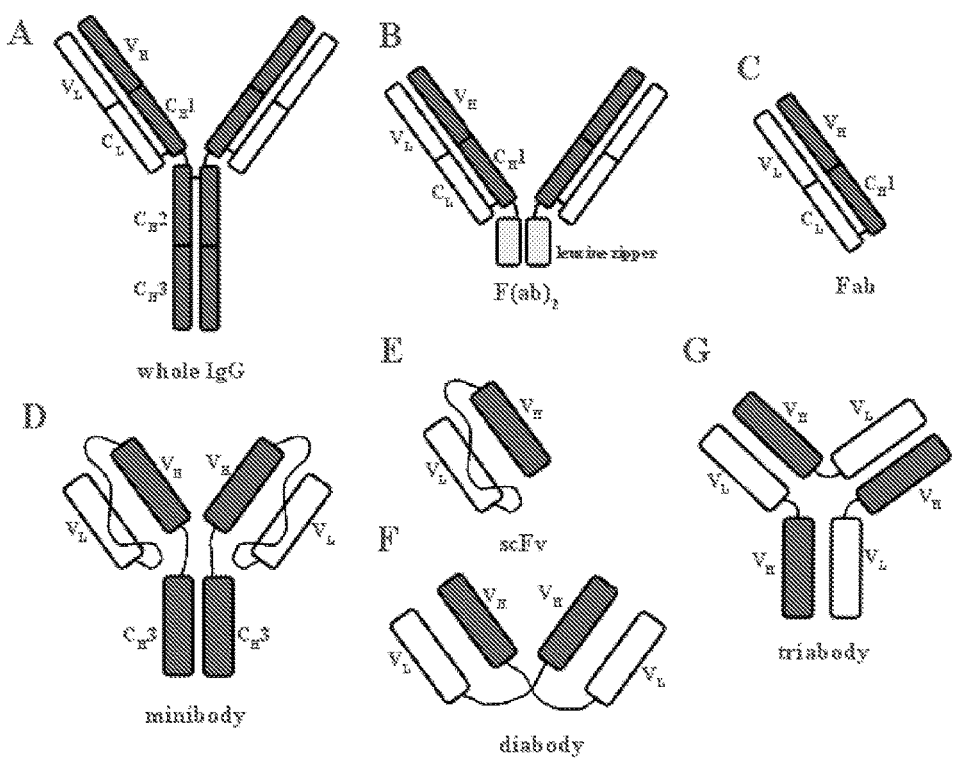

FIG. 3 shows a schematic representation of an IgG and its fragments and derivatives. FIG. 3A represents an whole IgG antibody. In FIG. 3B an $F(ab)_2$ and in FIG. 3C an Fab fragment is shown (removal of the Fc-fragment). The inclusion of a genetically engineered leucine zipper enables dimer association. Using recombinant technology the generation of smaller antibody fragments is possible. The single chain variable fragment (scFv, FIG. 3E) combines the $V_L$ and $V_H$ domains joined by a flexible synthetic linker sequence. The shortening of the linker sequence results in the formation of diabodies (FIG. 3F) and triabodies (FIG. 3G) or even tetrabodies (not shown). The scFv-fragment has been further modified to include constant domains of the antibody like the $C_H3$ domain resulting in the development of minibodies FIG. 3D.

Figure 4:
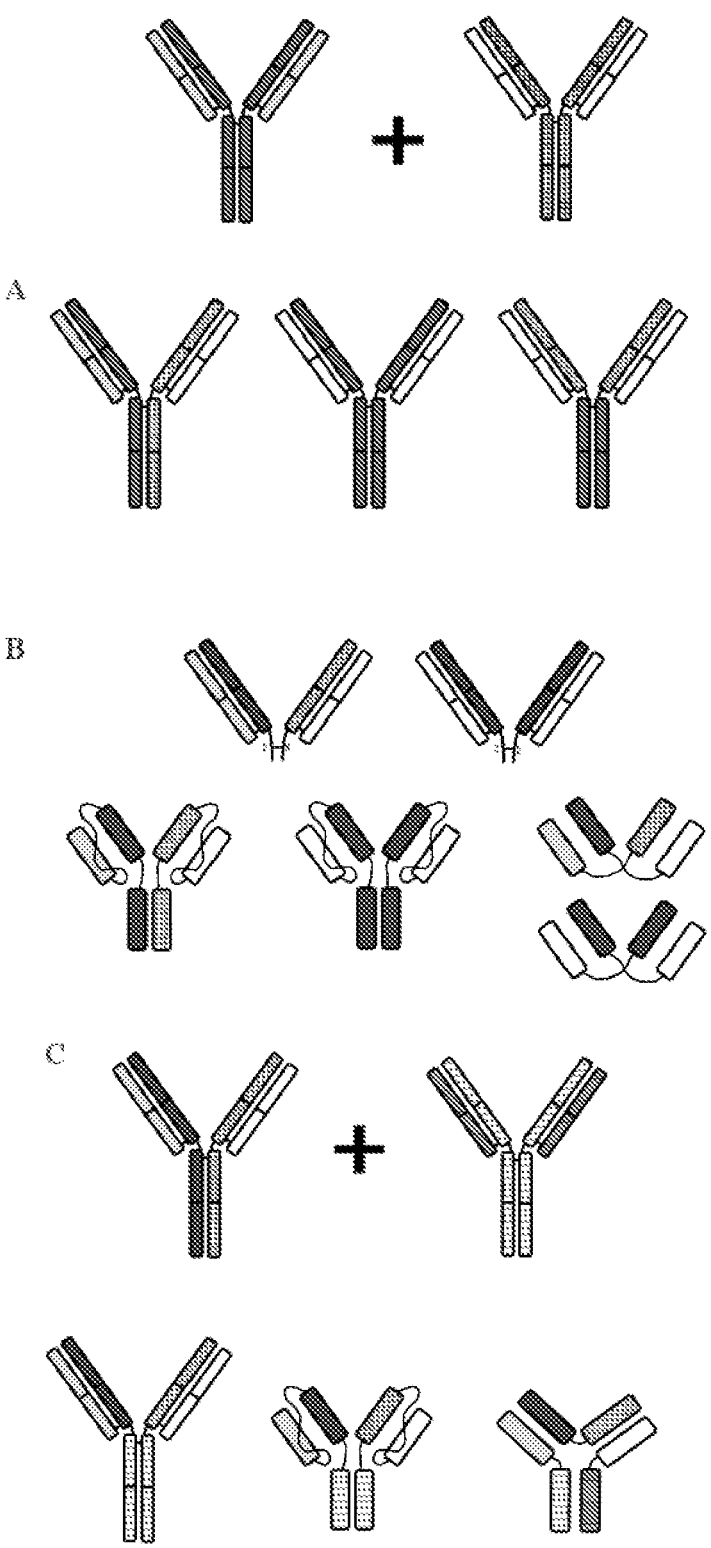

FIG. 4 shows a schematic representation of possible combinations of antibodies and antibody fragments to generate bi- and trivalent specificities. The combination of two different antibodies (e.g. antibody A and B) by mating stable transfected *Tetrahymena* cells results in different possible bispecific antibodies, shown in FIG. 4A. In FIG. 4B the possible combination of antibody fragments are shown resulting in different bi- and trispecific $F(ab)_2$ and dia- and minibodies. In FIG. 4C the possible combination of an antibody (e.g. antibody C) or antibody fragment with an bispecific antibody or antibody fragment by mating stable transfected *Tetrahymena* cells resulting in different possible tri- and multispecific antibodies and antibody fragments are shown.

FIG. 5A shows the expression plasmids for use in the ciliate *Tetrahymena thermophila* encoding the heavy and the light chain of the antibody is shown, representing the one plasmid approach. The plasmid contains an ampicillin (AmpR) and chloramphenical (CmR) resistance gene for selection in *E. coli*, a *T. thermophila* specific origin (rDNA ori) for plasmid stability in *T. thermopile*, a neomycin based selection cassette (NeoR) for identification of transformed ciliates and the two open reading frames of the target gene (heavy and light chain) under the control of an inducible promotor and followed by *T. thermophila's* [beta]-tubulin 2 terminator sequence (BTU2).

In FIGS. 5B and C expression plasmids are shown for the use in the ciliate *Tetrahymena thermophila* representing the two plasmid approach. In FIG. 5B the plasmid contains the 5' and 3' flanking regions of the *Tetrahymena* gene DHFR for directed integration of the heterologous gene, an ampicillin (AmpR) and chloramphenical (CmR) resistance gene for selection in *E. coli*, and a blasticidin S selection cassette (BsdR) for identification of transformed ciliates and the open reading frame of either the heavy or the light chain of the desired antibody under the control of an inducible promotor and followed by *T. thermophila's* [beta]-tubulin 2 terminator sequence (BTU2). In FIG. 5C the expression plasmid encoding the corresponding heavy or light chain of the antibody and containing the same features as listed for FIG. 5A.

FIG. 6 shows a schematic overview of the different stages in *Tetrahymena* conjugation. Conjugation process starts with pairing of cells homozygous for alternative alleles at one locus. The MIC (small circles) nested in but physically seperate from the MAC (large circles). The MICs undergo meiosis and generate four haploid nuclei, only one of them remains functional (anterior meiotic product) and the other three disintegrate. In this stage the meiotic crossover occurs, followed by the reciprocal exchange of the migratory pronuclei, which fuse with the stationary pronuclei of the recipient cell, forming the zygote nucleus. The zygote nucleus undergoes two mitotic divisions resulting in four different genetically identical diploid nuclei. At this stage the old MAC is degraded. Then the anterior products differentiate into new MACs and the posterior products remain diploid MICs. The cells separate (called now exconjugants) and undergo the first postzygotic cell division forming four karyonide cells. Each karyonide receives an independently differentiated new MAC and a mitotic copy of a functional MIC. Karyonides then begin vegetative multiplication by binary fission.

Figure 7:
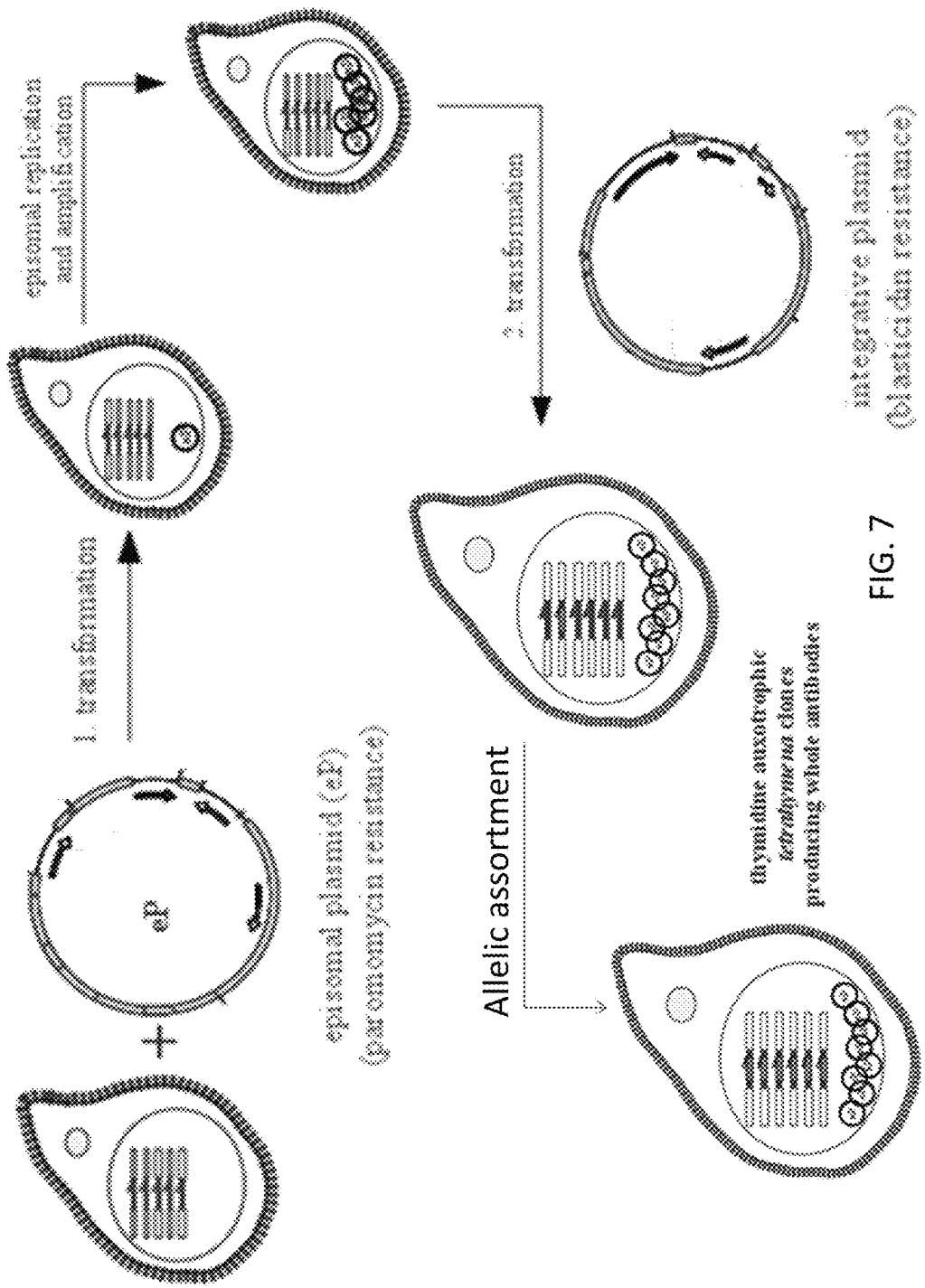

FIG. 7 shows a schematic overview of the transformation of *Tetrahymena* cells using one episomal and one integrative expression plasmid. This two plasmid approach leads to stable transfected *Tetrahymena* cells producing whole IgG and exhibit an thymidine auxotrophy.

FIG. 8 shows representative immunoblots of the anti-CD4 antibody Gk1.5 and it fragments expressed in *Tetrahymena thermophila* cells. In FIG. 8A, expression of Gk1.5 and its fragments in the cell pellet and in the supernatant of stable transformed cells is shown after different times of induction of the recombinant protein expression (p.i.) which were cultivated in a multifermenter (0.5 L labscale). The anti-CD4-antibody clone Gk1.5 from eBioscience served as a positive control. Staining took place using an Hrp-conjugated anti-rat-IgG. In FIG. 8B, a representative immunoblot of *Tetrahymena* expressed antibody Gk1.5 and its fragments after purification of the produced supernatant using a protein G column is shown.

FIG. 9 shows a comparison between codon usage in *Tetrahymena thermophila* and *Homo sapiens*. The latter is applicable for monoclonal antibodies, or fragments or derivatives thereof, being expressed in a mammalian cell line. See text for further explanations.

FIG. 10 shows the genetic code as used in cilates, particularly in *Tetrahymena*. The non-canonical nucleotide codes UAA and UAG, which encode for glutamine, are printed in bold. According to the general genetic code, these triplets are, however, stop codons (see striked through tripletts). "1LC" stands for "one letter code", whereas "3LC" stands for "three letter code".

REFERENCES

Tondravi, M M; Yao, M-C (1986): Transformation of *Tetrahymena thermophila* by microinjection of ribosomal RNA genes. PNAS 83, 4369-4373.

Gaertig, J; Gorovsky, M A (1992): Efficient mass transformation of *Tetrahymena thermophila* by electroporation of conjugants. PNAS 89, 9196-9200.

Cassidy-Hanley, D; Bowen, J; Lee, J H; Cole, E; VerPlank, L A; Gaertig, J; Gorovsky, M A;

Bruns, P J (1997): Germline and somatic transformation of mating *Tetrahymena thermophila* by particle bombardment. Genetics 146, 135-147.

Kufer, P; Lutterbüse, R; Baeuerle, P A (2004): A revival of bispecific antibodies. Trends in Biotechnology, Volume 22, Issue 5, 238-244, 1 May 2004

Ruf, P; Lindhofer, H (2001): Induction of a long-lasting antitumor immunity by a trifunctional bispecific Antibody. Blood, 15 Oct. 2001, Vol. 98, No. 8, pp. 2526-2534

Shields, R L et al, (2002): Lack of Fucose on Human IgG1 N-Linked Oligosaccharide Improves Binding to Human Fc RIII and Antibody-dependent Cellular Toxicity. J Biol Chem. Vol. 277, No. 30, pp. 26733-26740

Wei, Y et al, (2008) Glyco-engineering of human IgG1-Fc through combined yeast expression and in vitro chemoenzymatic glycosylation. Biochemistry 30; 47(39): 10294

Gerngross (2004): Advances in the production of human therapeutic proteins in yeasts and filamentous fungi. Nature Biotechnology 22 (11), 1409

Weide, T.; Bockau, U.; Rave, A.; Herrmann, L. & Hartmann, M. W. W.: A recombinase system facilitates cloning of expression cassettes in the ciliate *Tetrahymena thermophila*. BMC Microbiol, Vol. 7, pp. 12, 2007

Weide, T.; Herrmann, L.; Bockau, U.; Niebur, N.; Aldag, I.; Laroy, W.; Contreras, R.; Tiedtke, A. & Hartmann, M. W. W.: Secretion of functional human enzymes by *Tetrahymena thermophile*. BMC Biotechnol, Vol. 6, pp. 19, 2006

Banno, Y., Yano, K. & Nozawa, Y.: Purification and characterization of a secreted protease from *Tetrahymena pyriformis*. Eur J Biochem, Vol. 132(3), pp. 563-8, 1983

What is claimed is:

1. A full-length monoclonal Antibody (mAb), wherein the full-length mAb is glycosylated, wherein the glycosylated full-length mAb has an N-glycan structure that is fucose free, wherein the full-length mAb is produced by:
   1) with a system for the heterologous expression of the mAb, said system comprising
      a) at least one ciliate host cell, wherein the ciliate host cell is a member of the family Tetrahymenidae,
      b) incorporated, into said ciliate host cell, at least one heterologous nucleic acid molecule encoding said mAb, wherein the system further comprises a nucleic acid molecule encoding a signal sequence operably linked to said heterologous nucleic acid molecule, and
      c) culturing the host cell under conditions where the mAb is expressed and secreted into the extracellular medium under direction of the signal sequence;
   2) with a ciliate host cell obtained by conjugation of at least two ciliate host cells, wherein the ciliate host cell is a member of the family Tetrahymenidae, wherein the ciliate host cell has at least one heterologous nucleic acid molecule encoding said mAb, incorporated, wherein the ciliate host cell further comprises a nucleic acid molecule encoding a signal sequence operably linked to said heterologous nucleic acid molecule, and culturing the host cell under conditions where the mAb is expressed and secreted into the extracellular medium under direction of the signal sequence; or
   3) with a process for the production of the mAb, in a ciliate host cell, wherein the ciliate host cell is a member of the family Tetrahymenidae, said process comprising the steps of
      a) transfecting at least one ciliate host cell
         i) with at least one heterologous nucleic acid molecule encoding said mAb, wherein a nucleic acid molecule encoding a signal sequence is operably linked to said heterologous nucleic acid molecule, or
         ii) with at least one vector, wherein a vector for the transfection of a ciliate host cell is provided, said vector comprising at least one nucleic acid heterologous molecule encoding for the mAb and a nucleic acid molecule encoding a signal sequence is operably linked to said heterologous nucleic acid molecule, and
      b) culturing the host cell under conditions where the mAb is expressed and secreted into the extracellular medium under direction of the signal sequence.

2. The full-length mAb according to claim 1 which binds to at least one of the targets set forth in Table 1 (ADCC) or Table 3 (non ADCC).

3. The full-length mAb according to claim 1, which has at least one feature selected from the group consisting of increased ADCC, CDC, and/or Antibody-Dependent Apoptosis, extended serum half life, and/or bi, tri- or multispecifity.

4. A pharmaceutical composition comprising the full-length mAb according to claim 1.

* * * * *

SEQUENCE LISTING

```
<160> NUMBER OF SEQ ID NOS: 8

<210> SEQ ID NO 1
<211> LENGTH: 1416
<212> TYPE: DNA
<213> ORGANISM: Artificial
<220> FEATURE:
<223> OTHER INFORMATION: codon optimized nucleotide sequence of Gk1.5
      heavy chain

<400> SEQUENCE: 1
catatgaagt gttcttggat tatcctcttc cttatggctc ttaccactgg tgtcaattcc      60
gaagttcaac tccaataaga cggtgctgaa cttggtaagc ccggtacttc tgttaagctt     120
tcctgcaagg tttccgatta caacattaga agaacttata tgcactgggt caaccaaaga    180
cccggtaagg gtttggaatg gattggtaga attgatcctg ccaacggtaa cactatctat    240
ggtgaaaagt tcaagtctaa ggccaccttg actgctgaca cctcttccaa cactgcttac    300
```

```
atgcaattgt ctcaattgaa gtccgacgat actgctattt atttctgtgc catcggtgtc    360
caatacctcg attactgggg tcaaggtgtt atggtcaccg tctcctctgc ttaaaccact    420
gctccctctg tttacccct cgctcctggt tgcggtgata ccacttcttc cactgttact    480
ttgggttgcc tcgtcaaggg ttatttcccc gaacccgtta ctgtcacctg gaactccggt    540
gccttatctt ccgacgttca cactttccct gctgttttac aatctggtct ttacaccctc    600
acttcttccg ttacctcctc tacctggccc tcccaaaccg tcacttgtaa cgtcgctcac    660
cctgcttctt ccaccaaggt cgataagaag gtcgaaagaa gaaacggtgg tatcggtcac    720
aagtgcccca cctgtcctac ctgccacaag tgccccgtcc ccgaattatt gggtggtcct    780
tccgtcttca ttttccccc taagcccaag gatatcttac ttatttctta aaacgctaag    840
gtcacttgcg ttgtcgttga tgtttctgaa gaagaacctg acgtttaatt ctcttggttc    900
gtcaacaatg ttgaagtcca caccgcttaa acccaaccca gagaagaata atacaactct    960
actttcagag tcgtttctgc tttacctatc aacactaag attggatgtc cggtaaggaa    1020
ttcaagtgta aggtcaacaa taaggctctc ccctctccta tcgaaaagac catttccaag   1080
cctaagggtc tcgttagaaa gccccaagtt tacgttatgg gtcccctac cgaacaactc    1140
actgaacaaa ctgtttcctt aacttgctta acctccggtt tcttgcccaa cgatatcggt    1200
gttgaatgga cctccaatgg tcacatcgaa aagaactaca agaacaccga acctgtcatg    1260
gactccgatg gttctttctt catgtactct aagcttaacg tcgaaagatc cagatgggat    1320
tccagagccc ccttcgtttg ctccgtcgtc cacgaaggtt tacacaacca ccacgtcgaa   1380
aagtctatct ctagacccccc cggtaagtga agatct                            1416

<210> SEQ ID NO 2
<211> LENGTH: 708
<212> TYPE: DNA
<213> ORGANISM: Artificial
<220> FEATURE:
<223> OTHER INFORMATION: codon optimized nucleotide sequence of Gk1.5
      kappa light chain

<400> SEQUENCE: 2
atggaaactg atagattatt gctctgggtc ttacttttat gggtccccga ctctaccggt     60
gataccgtcc tcacttaatc tcctgcttta gctgtctctc tggtgaaag agttaccatc    120
tcctgcagag ctactgaaag attctctact cttatccact ggttacaaca agacctggt     180
caacaaccca agttgctat ttacttgacc tcccacttag attctggtgt tcccgctaga    240
ttctccggtt ctggttctgg tactgacttc acccttacca ttgaccctgt tgaagctgat    300
gatactgcta cctactactg ctaataaacc tggaacgatc cctggacctt cggtggtggt    360
actaagctcg aactcaagag agccgatgcc gctcccactg tttccatctt ccctccctct    420
actgaataac ttgctaccgg tggtgcttct gtcgtttgct tgatgaataa cttctacccc    480
agagacattt ctgttaagtg gaagatcgac ggtaccgaaa gaagagatgg tgtcctcgat    540
tccgtcaccg atcaagattc caaggactcc acttattcca tgtcctctac tctctctctc    600
actaaggccg attacgaatc tcacaacttg tataacctgcg aagttgtcca caagacttcc    660
tcctcccccg tcgttaagtc cttcaacaga acgaatgtt gaagatct                  708

<210> SEQ ID NO 3
<211> LENGTH: 135
<212> TYPE: PRT
<213> ORGANISM: Artificial
```

```
<220> FEATURE:
<223> OTHER INFORMATION: amino acid sequence encoded by Sequence No.1

<400> SEQUENCE: 3

Met Lys Cys Ser Trp Ile Ile Leu Phe Leu Met Ala Leu Thr Thr Gly
1               5                   10                  15

Val Asn Ser Glu Val Gln Leu Gln Gln Asp Gly Ala Glu Leu Gly Lys
            20                  25                  30

Pro Gly Thr Ser Val Lys Leu Ser Cys Lys Val Ser Asp Tyr Asn Ile
        35                  40                  45

Arg Arg Thr Tyr Met His Trp Val Asn Gln Arg Pro Gly Lys Gly Leu
50                  55                  60

Glu Trp Ile Gly Arg Ile Asp Pro Ala Asn Gly Asn Thr Ile Tyr Gly
65                  70                  75                  80

Glu Lys Phe Lys Ser Lys Ala Thr Leu Thr Ala Asp Thr Ser Ser Asn
                85                  90                  95

Thr Ala Tyr Met Gln Leu Ser Gln Leu Lys Ser Asp Asp Thr Ala Ile
            100                 105                 110

Tyr Phe Cys Ala Ile Gly Val Gln Tyr Leu Asp Tyr Trp Gly Gln Gly
        115                 120                 125

Val Met Val Thr Val Ser Ser
    130                 135

<210> SEQ ID NO 4
<211> LENGTH: 127
<212> TYPE: PRT
<213> ORGANISM: Artificial
<220> FEATURE:
<223> OTHER INFORMATION: amino acid sequence sequence encoded by
      Sequence No.2

<400> SEQUENCE: 4

Met Glu Thr Asp Arg Leu Leu Leu Trp Val Leu Leu Leu Trp Val Pro
1               5                   10                  15

Asp Ser Thr Gly Asp Thr Val Leu Thr Gln Ser Pro Ala Leu Ala Val
            20                  25                  30

Ser Pro Gly Glu Arg Val Thr Ile Ser Cys Arg Ala Thr Glu Arg Phe
        35                  40                  45

Ser Thr Leu Ile His Trp Leu Gln Gln Arg Pro Gly Gln Gln Pro Lys
50                  55                  60

Leu Leu Ile Tyr Leu Thr Ser His Leu Asp Ser Gly Val Pro Ala Arg
65                  70                  75                  80

Phe Ser Gly Ser Gly Ser Gly Thr Asp Phe Thr Leu Thr Ile Asp Pro
                85                  90                  95

Val Glu Ala Asp Asp Thr Ala Thr Tyr Tyr Cys Gln Gln Thr Trp Asn
            100                 105                 110

Asp Pro Trp Thr Phe Gly Gly Gly Thr Lys Leu Glu Leu Lys Arg
        115                 120                 125

<210> SEQ ID NO 5
<211> LENGTH: 60
<212> TYPE: DNA
<213> ORGANISM: Artificial
<220> FEATURE:
<223> OTHER INFORMATION: codon optimized nucleotide sequence of
      endogenous Gk1.5 heavy chain signal peptide

<400> SEQUENCE: 5
catatgaagt gttcttggat tatcctcttc cttatggctc ttaccactgg tgtcaattcc      60
```

```
<210> SEQ ID NO 6
<211> LENGTH: 19
<212> TYPE: PRT
<213> ORGANISM: Artificial
<220> FEATURE:
<223> OTHER INFORMATION: amino acid sequence sequence encoded by
      Sequence No.5

<400> SEQUENCE: 6

Met Lys Cys Ser Trp Ile Ile Leu Phe Leu Met Ala Leu Thr Thr Gly
1               5                   10                  15

Val Asn Ser

<210> SEQ ID NO 7
<211> LENGTH: 60
<212> TYPE: DNA
<213> ORGANISM: Artificial
<220> FEATURE:
<223> OTHER INFORMATION: codon optimized nucleotide sequence of
      endogenous Gk1.5 kappa light chain signal peptide

<400> SEQUENCE: 7
atggaaactg atagattatt gctctgggtc ttacttttat gggtccccga ctctaccggt      60

<210> SEQ ID NO 8
<211> LENGTH: 20
<212> TYPE: PRT
<213> ORGANISM: Artificial
<220> FEATURE:
<223> OTHER INFORMATION: amino acid sequence encoded by Sequence No.7

<400> SEQUENCE: 8

Met Glu Thr Asp Arg Leu Leu Leu Trp Val Leu Leu Leu Trp Val Pro
1               5                   10                  15

Asp Ser Thr Gly
            20
```